(12) United States Patent
Russell

(10) Patent No.: US 7,127,826 B2
(45) Date of Patent: Oct. 31, 2006

(54) MARKERS, METHODS OF MARKING, AND MARKING SYSTEMS FOR USE IN ASSOCIATION WITH IMAGES

(76) Inventor: Donald G. Russell, 86 Windsor Rd., Kensington, CT (US) 06037

( * ) Notice: Subject to any disclaimer, the term of this patent is extended or adjusted under 35 U.S.C. 154(b) by 0 days.

(21) Appl. No.: 10/722,920

(22) Filed: Nov. 26, 2003

(65) Prior Publication Data
US 2005/0000133 A1    Jan. 6, 2005

Related U.S. Application Data

(60) Provisional application No. 60/429,943, filed on Nov. 29, 2002.

(51) Int. Cl.
*B43L 13/20* (2006.01)
(52) U.S. Cl. .............. 33/758; 33/512; 33/566
(58) Field of Classification Search ............. 33/566, 33/511–512, 758
See application file for complete search history.

(56) References Cited

U.S. PATENT DOCUMENTS

| 3,583,358 A | 6/1971 | Hanson, Jr. |
|---|---|---|
| 3,924,879 A | 12/1975 | Wright |
| 4,015,034 A | 3/1977 | Smolen |
| 4,274,006 A | 6/1981 | Caine |
| 4,353,759 A | 10/1982 | Stallings |
| 4,425,391 A | 1/1984 | Wilson |
| 4,680,210 A | 7/1987 | Corcoran |
| 4,698,836 A | 10/1987 | Minasian |
| 4,764,948 A | 8/1988 | Hurwitz |
| 4,951,595 A | 8/1990 | Bedford, Jr. |
| 4,953,193 A | 8/1990 | Robinson |
| 4,985,019 A * | 1/1991 | Michelson .................. 604/180 |
| 5,052,035 A * | 9/1991 | Krupnick .................... 378/163 |
| 5,101,756 A | 4/1992 | Strumbos |
| 5,287,397 A | 2/1994 | Dumsha |

(Continued)

FOREIGN PATENT DOCUMENTS

EP    0 545 959 B1    11/1994

(Continued)

*Primary Examiner*—Yaritza Guadalupe-McCall
(74) *Attorney, Agent, or Firm*—McCarter & English, LLP

(57) ABSTRACT

Markers, methods of marking, and marking systems for use in association with images are disclosed. One marker is removable with a targeted design and metric dimensions inscribed on a clear plastic flap. This marker is attached adjacent to an area of interest with the target placed in such a manner to precisely pin point out an observed abnormality. A paper label at one edge is available for written comments and directions for further studies. The marker can be removed without damage to the image(s).

41 Claims, 24 Drawing Sheets

U.S. PATENT DOCUMENTS

| | | |
|---|---|---|
| 5,323,443 A | 6/1994 | Lary |
| 5,368,030 A | 11/1994 | Zinreich et al. |
| 5,469,847 A | 11/1995 | Zinreich et al. |
| 5,702,128 A * | 12/1997 | Maxim et al. ............... 283/81 |
| 5,732,122 A | 3/1998 | Tibbals |
| 5,848,125 A | 12/1998 | Arnett |
| 6,063,225 A * | 5/2000 | Riordan ..................... 156/250 |
| 6,145,722 A * | 11/2000 | Behrens et al. ............... 225/42 |
| 6,198,807 B1 | 3/2001 | DeSena |
| 6,231,508 B1 | 5/2001 | Miller et al. |
| 6,354,737 B1 | 3/2002 | Hufe et al. |
| 6,356,621 B1 | 3/2002 | Furumori et al. |
| 6,540,756 B1 | 4/2003 | Vaughan |
| 6,544,185 B1 * | 4/2003 | Montegrande ............... 600/458 |
| 6,826,257 B1 * | 11/2004 | Sayre et al. ................ 378/163 |
| 2002/0082948 A1 | 6/2002 | Panelli |
| 2002/0151797 A1 * | 10/2002 | Montegrande ............... 600/458 |
| 2003/0182815 A1 | 10/2003 | Carlson, II |
| 2004/0056478 A1 * | 3/2004 | Bruce ......................... 283/81 |
| 2004/0116802 A1 * | 6/2004 | Jessop et al. ............... 600/414 |

FOREIGN PATENT DOCUMENTS

| | | |
|---|---|---|
| EP | 0 648 610 B1 | 6/1998 |
| EP | 0 984 864 B1 | 7/2002 |
| JP | 10165391 A | 6/1998 |

* cited by examiner

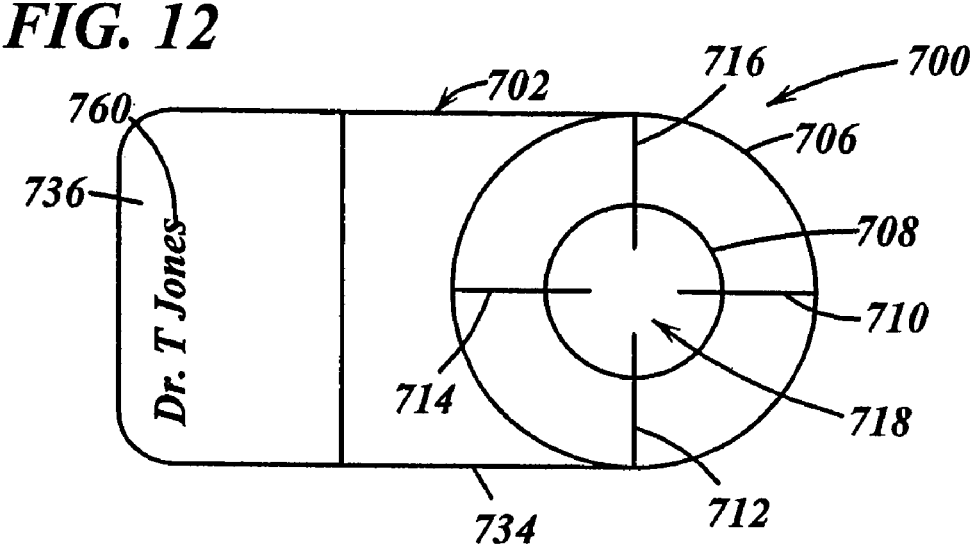
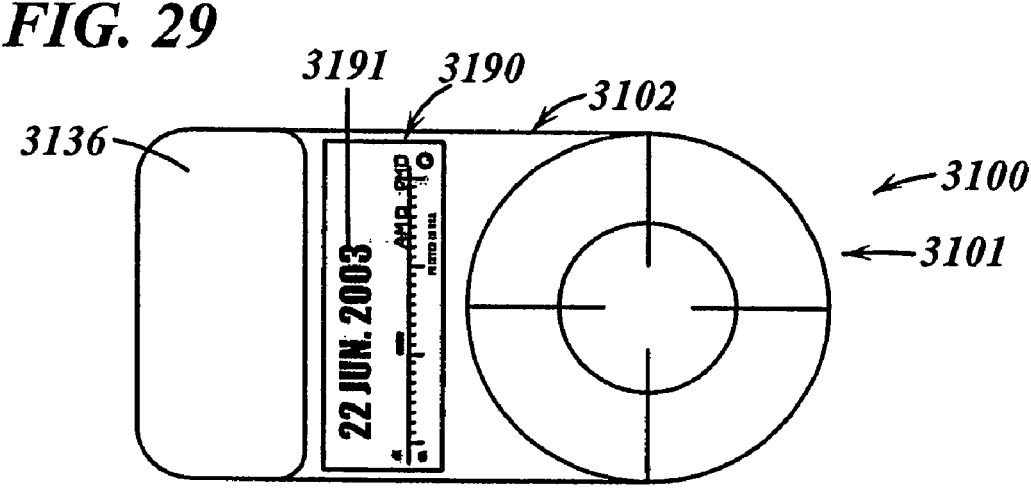
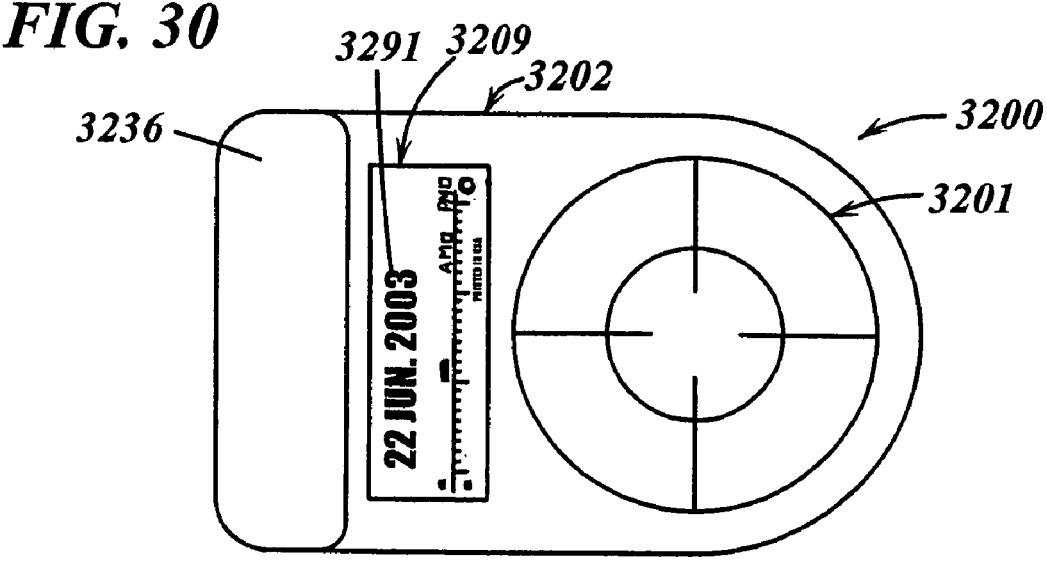

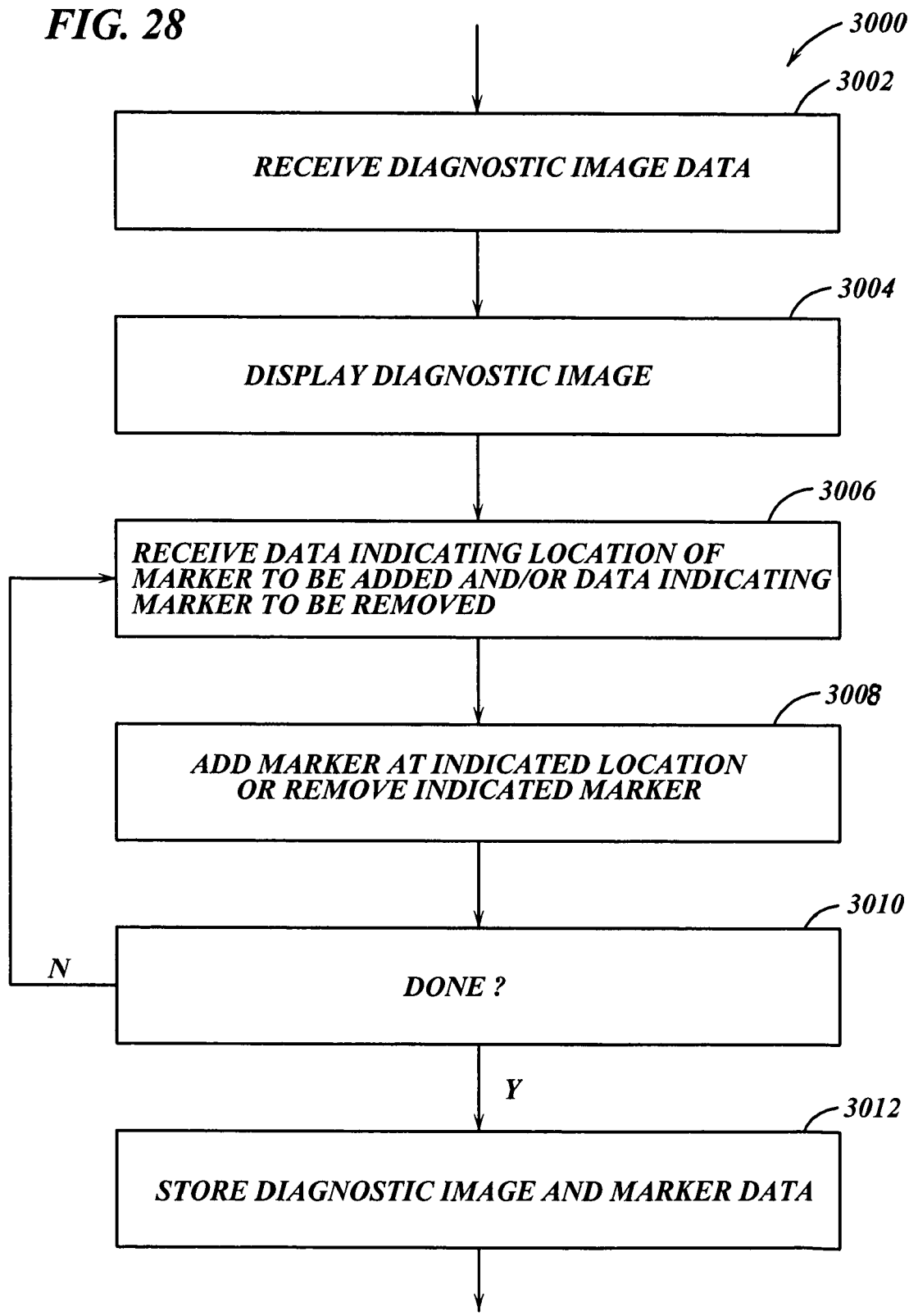

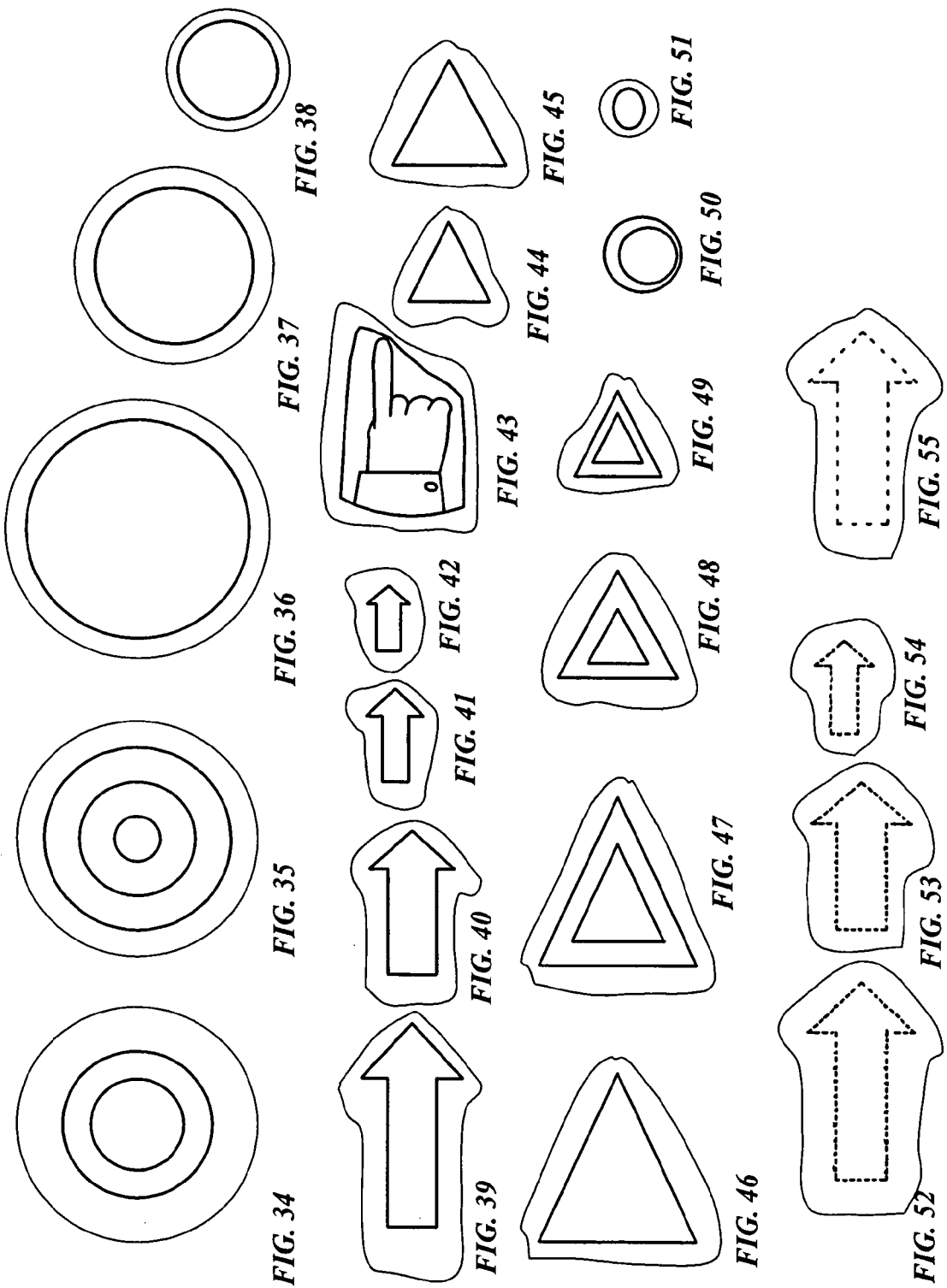

MARKERS, METHODS OF MARKING, AND MARKING SYSTEMS FOR USE IN ASSOCIATION WITH IMAGES

CROSS REFERENCE TO RELATED APPLICATIONS

This application claims priority to U.S. Provisional Patent Application Ser. No. 60/429,943, filed Nov. 29, 2002, entitled "MARKERS AND MARKER METHODS FOR DIAGNOSTIC IMAGES, AND SYSTEMS AND APPARATUS, AND METHODS EMPLOYING SAME", which is incorporated by reference herein.

RELATED INFORMATION

Diagnostic images in medical practice are often radiographic shadows of anatomic components representing a graphic display of disparate radiographic densities. This array of contrasting anatomic shadows is commonly captured and displayed on a photographic film base for study by an observer on a lighted view box. These are the well known diagnostic radiographs or x-ray studies interpreted by a physician trained in this field as a Radiologist.

Study of these radiographic images involves an extensive knowledge of the normal anatomic shadows in order to detect abnormal pathology as defined by distortion of the normal pattern or the presence of incompatible or inappropriate shadows. Often the abnormality is a significant visual abnormality that is immediately evident. An example of this might be a grossly fractured bone.

Furthermore, the site of the abnormality is frequently explicitly evident and is described in relationship to the right or left side of the patient and the proximal or distal portion of the bone injured. As per the example above, the fractured bone may be an easily seen fracture of neck or proximal portion of the femur.

In a similar context, an area of pathology may be described by its relationship or the proximity to a well defined normal organ. Additional description, as an aid in identifying a finding, may include the size and/or shape of the abnormality. For example, a description may read "There is a poorly defined, soft tissue nodule in the left lower lobe as seen on the PA view of the chest. This nodule is adjacent to the left border of the heart and measures 2 centimeters in diameter."

It is readily evident that conveying sufficient information on a report to enable subsequent observers to unequivocally locate an imaged abnormality requires extensive use of adjacent anatomic landmarks, specific descriptive terms of the size and nature of the observed finding and references to the relative position within the imaged body part.

If, however, the finding is small, difficult to see, or is superimposed on a confusing radiographic background some additional applied mark on the image may be extremely useful to clearly and immediately locate and identify the finding.

Furthermore, if the surrounding anatomic tissue does not have clearly defined anatomic reference points, a description of the location within said organ may be imprecise and confusing to a second observer.

In the event that the abnormality is difficult to perceive and/or the exact site cannot be precisely described, it is often very useful to place some mark on the image adjacent to or encircling the area of concern. It should be emphasized that several other medical specialists not trained in radiology are brought into most cases to do further diagnostic studies, render consultation, undertake biopsy and possibly perform surgical extirpation. The use of a mark on an important image enhances immediate visual communication and eliminates confusion, ambiguity, and uncertainty.

A common method of marking the surface of a film image is to use a wax pencil, usually black. The presence of an applied mark will make it possible for all the other observers to immediately focus on the abnormality in question. Possible errors relating to imprecise description and uncertainty will be avoided permitting an accurate and expeditious diagnosis and treatment.

As useful as a specific mark applied on an image may be, many radiologists hesitate to apply any mark onto an image because of the many draw backs and disadvantages that are inherent in this act. For example, if a mark is opaque or semi-opaque, it may obscure image details that are under the mark. In addition, marks are sometimes seen as an aberration and/or a disconcerting distraction to the reader, such that the eye of the reader is drawn to the mark during the study of the remainder of the image or during an attempt to compare the marked image to prior films of the same area or to additional or contra lateral views of the same body part. Further, a film marked with a wax pencil is handled with other films or put into the envelope, specks of the wax may be transferred onto adjacent films. As a result, wax artifacts may be implanted onto other images. In addition, the meaning or intent of a mark may not be evident unless the originator of the mark verbally explains it or makes specific reference to the applied mark in a report. An image mark without a clearly stated meaning represents another problem for a later observer to resolve. Moreover, marks made using a wax are not easily removed. Attempts at removal most often involve time consuming scrubbing of the film surface with the finger or rubbing the mark off with a tissue. Against the customary dark film background, it is, furthermore, virtually impossible to be sure that all of the wax has been removed. Still further, a rubbing action on the surface of a film can scratch the emulsion and the film base and result in permanent damage to the image. Furthermore, if film images are to be digitized for storage or for transmission to a remote location for consultation, comparison, or further study, wax markings must be completely removed or the digitized image will reflect the presence of the mark. Unless completely removed, film marks, as well as residual wax remnants, become a permanent part of the digital image and the image detail beneath often cannot be electronically reconstituted. If the image is to be digitized for a Computer Assisted Diagnostic review system, wax marks have to be completely removed before the film image is recorded electronically. Any marks on the surface of the film may be confused with actual shadows present within the film emulsion itself. Finally, medical diagnostic images are precious and irreplaceable records of the patient as of the moment in time they were obtained and/or may show an anatomic part in a position and projection that can never be exactly reproduced.

For all of the reasons stated above, with emphasis on the sanctity of these images, many professionals in the radiological field strongly resist the temptation to deface and degrade an image with an anonymous surface mark that cannot be easily and completely removed.

These issues are now further addressed with respect to mammography or radiographic imaging of breast tissue. Mammography has developed to a point where the images are captured in most exquisite detail. Positioning and breast compression are carefully and intricately applied. Standard views are specifically and routinely obtained. Special x-ray tubes with minute focal spots produce filtered low kilovoltage x-rays that permit registration of excellent detail of the breast soft tissues. Film handling and development is consistently monitored for quality and consistency. Mammography centers, in order to be accepted and certified by The American College of Radiology, must exercise all of the specified technical aspects of this imaging science to deliver flawless and immaculate images which leads to consistent, concise and explicit interpretation. These are among the finest radiographic records in the practice of diagnostic imaging. Considering the detailed information that is captured and enduringly preserved, marking the image with any element of permanency is not a decision that can be taken lightly.

There are, in the process of interpreting mammograms, many times when it would be of extreme benefit to place some mark on the image to specifically identify and locate the exact position of a subtle finding. The breast has no natural landmarks except the nipple, which is projected in profile on the standard views. The relative position of a small mass or some suspicious finding is usually described as in one of the four quadrants of a specific projection, with the quadrant lines centered on the nipple. The radial distance from the nipple added to the report to further expedite finding the location of the abnormality.

Dictating the size, configuration, and general area of an ill defined mammography finding is, at best, imprecise communication. Many cases require repeated study by a host of subsequent observers who are often challenged to clearly identify an elusive finding on a film. This work can be a misuse of valuable time spent searching for an area of concern and the resulting confusion can lead to delay in care of the patient and possible error in treatment.

Accordingly, it would be desirable to provide a method for marking an image that overcomes one or more of the above described drawbacks.

SUMMARY

According to a first aspect of the present invention, a substrate having at least one portion with an adhesive backing and having at least one portion that is substantially transparent and has indicia for identifying or measuring details of an image on which the marker is to be overlayed.

According to another aspect of the present invention, apparatus comprises a light transmitting substrate for providing an image and a removable marker attached to the substrate. The removable marker has a first portion with adhesive backing for attachment to the light transmitting substrate and further has a second portion that is substantially transparent and without adhesive backing thereby allowing the second portion to be lifted from the light transmitting substrate, without the need to lift the adhesive backed portion.

According to another aspect of the present invention, apparatus comprises a light transmitting substrate for providing an image and a removable marker attached to the substrate. The removable marker has a first portion with adhesive backing for attachment to the light transmitting substrate and further has a second portion that is substantially transparent and has a target sight inscribed thereon.

According to another aspect of the present invention, apparatus comprises a light transmitting substrate for providing an image and a removable marker attached to the substrate. The removable marker has a first portion with adhesive backing for attachment to the light transmitting substrate and further has a second portion that is substantially transparent, wherein at least one of the first portion and the second portion includes a gauge portion.

According to another aspect of the present invention, apparatus comprises a light transmitting substrate for providing an image and a removable marker attached to the substrate. The removable marker has a first portion with adhesive backing for attachment to the light transmitting substrate and further has a second portion that is substantially transparent, wherein the first portion includes a paper surface for receiving writing.

According to another aspect of the present invention, a system comprises a processor to receive information that represents an image and information that indicates a desired location within the image for addition of a marker, and to provide information that represents the image and the marker added at the desired location.

According to another aspect of the present invention, apparatus comprises a holder and a plurality of markers releasably mounted in the holder.

One advantage of currently preferred embodiments of the above aspects of the present invention is that they provide a method for marking diagnostic images to identify features or areas of interest without causing any substantial damage to the diagnostic image.

In one currently preferred embodiment, a marker has an adhesive base tab for attaching the marker to the surface of an image (e.g., a diagnostic image). The tab has a paper surface to permit the addition of a written note explaining the meaning or intent of an applied marker. A precise target or gun sight localizer is inscribed on a clear film in the form of an extension attached to the adhesive tab. The center of the target may be placed directly over the area of visual interest and is held in place by the attached adhesive tab. The target has metric dimensions wherein the observer may estimate, with some precision, the size of an observed abnormality. The target itself, not being adherent itself to the film, may be temporarily lifted for closer examination of the area of interest without disturbing the adhesive base tab. If required, the marker, including the written message, may be left in place when the film image is place in the envelope for indefinite storage. This inscribed marker may, for example, inform all future observers as to exact location the area of concern as of the date of the exam and the reason for application of this defining marker. The entire marker may, at any time, be immediately removed, finally or temporarily, with no residual mark or damage to the image or injury to the emulsion or film base. Such markers, which may have various forms, and is used as described as an adhesive, non-damaging, removable, inscribable image marker, may be used in the study and/or analysis of radiographic film images or in any other informational system or display where there is a need to specifically and/or unambiguously identify some visualized area of interest.

It should be understood that although many of the images described herein are diagnostic images, the various aspects of the present invention may be used in association with any type of image, unless explicitly stated otherwise. For example markers may be used in association with any type of image that conveys information and is to be analyzed, including but not limited to architectural or mechanical drawings, electrical schematics, photographs and graphic art.

As to diagnostic images, it should be understood that although diagnostic images are widely employed within the medical fields, diagnostic images are also used in a wide variety of fields outside the medical field.

It should be further understood that images may come in many forms and may for example be captured on a light transmitting substrate (e.g., x-ray film), plastic, paper or any other suitable medium. Unless explicitly stated otherwise, the various aspects of the present invention are not restricted to use in association with light transmitting substrates (e.g., x-ray films).

Other embodiments and aspects of the present invention will be apparent in view of the drawings and detailed description hereinafter.

BRIEF DESCRIPTION OF THE DRAWINGS

FIGS. 12–22 show elevational views of removable markers in accordance with further embodiments of one aspect of the present invention;

FIG. 28 is a flowchart showing steps carried out in one embodiment of the data processor of FIG. 26, in association with adding and/or removing markers from a digital diagnostic image displayed on a display device;

FIGS. 29–33 show elevational views of removable markers in accordance with further embodiments of one aspect of the present invention;

FIGS. 34–55 show elevational views of removable markers in accordance with further embodiments of one aspect of the present invention;

DETAILED DESCRIPTION

Figure 1:
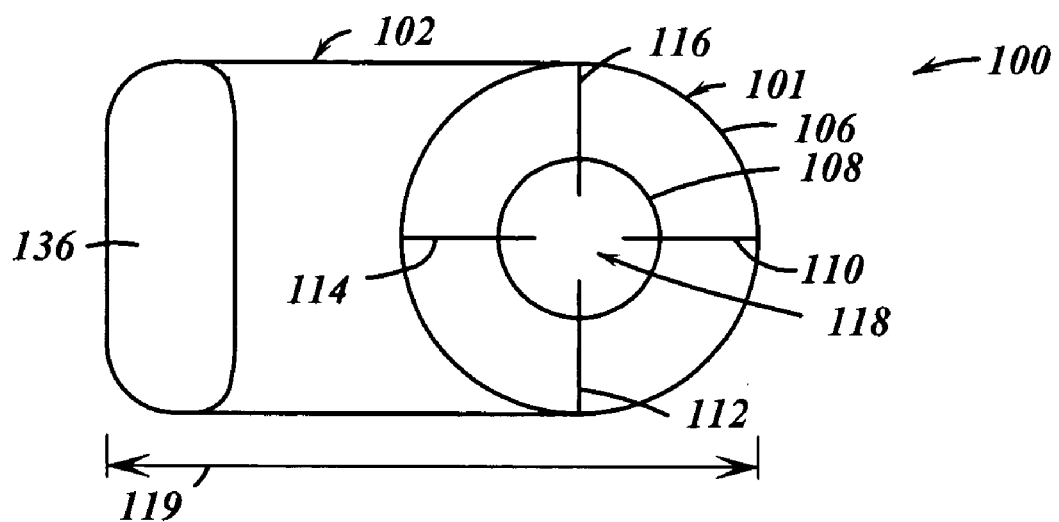
FIG. 1 shows an elevational view of a removable marker in accordance with one embodiment of one aspect of the present invention.

FIG. 1 shows a marker 100 in accordance with one embodiment of one aspect of the present invention. This marker 100 is adapted to be removably attached to an image, for example, a diagnostic image captured on a radiographic film or printed on paper, for any of various purposes, for example, but not limited to, identification, clarification, emphasis of one or more aspects of the image, and/or combinations thereof.

The marker 100 includes a base (or substrate) 102 that comprises a clear, thin plastic sheet of an appropriate size and shape. The marker 100 is inscribed with a target sight 101 to aid, for example, in precisely identifying a feature of interest and/or a center of a site of interest within the image. The target site comprises a series of concentric circles 106, 108 and cross hairs (e.g., formed of line segments 110, 112, 114 and 116).

It is often desirable to make the line thickness of the target sight 101 as thin as possible so as not to obscure any features of the portion of the image underlying the marker.

The embodiment of the marker illustrated in FIG. 1 has rounded (i.e., radiused) corners to help keep the marker from being struck by and/or getting caught on objects, the occurrence of which could cause the marker to become detached from an image.

Figure 2:
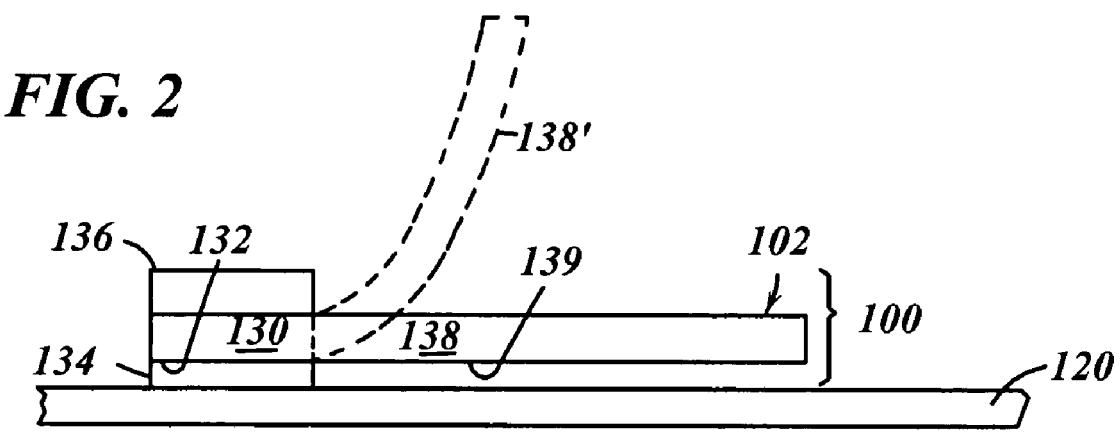
FIG. 2 shows a side elevational view of the marker of FIG. 1.

FIG. 2 shows a side elevational view of the marker 100 and a diagnostic image 120 (for example, a radiographic image). The base 102 of the marker 100 has a first portion 130 with an underside (or backing) 132 that is coated with an adhesive layer 134 that removably attaches or releasably secures the marker 100 to the image 120 and enables the marker 100 to stay in place on the image 120 under ordinary handling conditions. However, the marker 100 may be removed entirely without damaging or leaving residual glue on the diagnostic image 120.

In some embodiments, the marker 100 has a length 119 of about 6 cm, the circle 106 and the circle 108 have diameters of 4 centimeters (cm) and 2 cm, respectively, and each of the line segments has a length of 1.5 cm, thereby leaving an area 118, without indicia, near the center of the circle 108.

It should be understood however, that the marker can be made any size. For example, images used in dental applications are often relatively small compared to that of a mammogram. Thus, it may be desirable to employ a marker that has reduced size compared to the marker of FIGS. 1–2. On the other hand, images of some large body parts may be relatively large compared to the size of a mammogram. Thus, it may be desirable to employ a marker that has increased size compared to the marker of FIGS. 1–2.

In some embodiments, a size increase or decrease is carried out using a scaling factor, e.g., 4:1 or 1:4, respectively, in order to preserve the relative proportioning of the features of a marker, although this is not required.

Notwithstanding the above, there is no requirement that the markers have a particular size compared to the size of the images to be marked.

Notes and communications pertaining to an observed oddity or orders for further procedures may be recorded in pen or pencil on a note portion, which may be, for example, a plain paper tab 136 is attached to the base 102 over the area of the adhesive 134.

The base 102 has a second portion 138 with an underside 139 that is free (or substantially free) of adhesive and therefore may be lifted upward (e.g., as represented by dotted lines 138') to further study the portion of the diagnostic image 120 that is overlayed by the second portion 138 without any need for shifting or relocating the marker 100.

As stated above, the marker 100 may be left in place for any length of time or removed completely leaving no residual adhesive and without damage to the film or emulsion.

The adhesive material(s) may be for example a pressure sensitive adhesive. One method for forming the adhesive layer is to coat the surface 132 with an adhesive material in liquid form. Another method is to apply an adhesive material in a dry form. Dry adhesive suitable for use as a layer or backing may be obtained in large sheets and then cut to size. It may be desirable to select the adhesive material(s) based at least in part on the type of image with which a marker is to be used.

Markers may for example be provided in the form of a stack (for example as described with respect to FIG. 23), on a sheet, or in an individually separate form. Markers that are provided in an individually separate form may be provided with a releasable backing attached to the adhesive layer (for example as shown by dotted lines 335 in FIG. 5). Such a backing helps keep the markers from sticking to one another prior to use and would need to be removed prior to releasably attaching the marker to an image. Such a backing may be formed of a paper, a coated paper or a plastic material that permits the backing to be manually peeled away from the adhesive in order to expose the adhesive prior to attaching the marker to an image. Markers provided in a stack or on a sheet would be removed (e.g., "peeled") off the stack or sheet prior to use. In some embodiments, a plurality of markers are disposed on an elongated releasable backing rolled into a cylindrical form.

Although the marker 100 is disclosed as having an adhesive layer, this is not meant to imply that the adhesive must have a particular configuration or be uniformly disposed on the surface 132. For example, in some embodiments, adhesive may be disposed on only a portion of the surface 132. In some embodiments, the adhesive disposed on the surface 132 may have a grid or grid-like form. In some other embodiments, the adhesive may be in the form of an array of circles. In some other embodiments, the adhesive may be disposed only along one or more edges of the surface 132 or one or more portions of such edges. In some other embodiments, the adhesive disposed on the surface 132 may have an irregular configuration and/or any combination of the configurations.

Moreover, it should be understood that the lines on the marker can be any color.

A marker of this type may be used for example, in association with images captured on light transmitting substrate (e.g., film) or printed on paper. The marker can be used to help point out areas of concern on old films as well as expediting the identification of these specific areas of concern on newer films, and thereby facilitating a succinct and specific comparison report.

The marker is particularly attractive in the field of mammography, as further described hereinafter. However, markers of this type may be used on any type of image, including but not limited to, for example, radiological images, where there is a need to precisely point out a feature of interest (e.g., an abnormality). The image may be on a translucent substrate (e.g., x-ray film), paper, or any other medium suitable for the particular application.

The marker is also particularly attractive for use in association with computerized tomagraphy (commonly referred to as CT), magnetic resonance imaging (commonly referred to as MRI), ultrasound and nuclear medicine (gamma camera depictions), which often involve a group or series of images to be evaluated. For example, a marker of this type may be used as an aid in defining the specific images which show a lesion on a series of images of a large number such as a complete set of CT or MRI slices. A marker could also be made indicating views referred to in the report on a series of ultrasound images or nuclear medicine gamma camera depictions. Note that CT is often used to produce images of axial sections of a body. MRI is often used to image axial, coronial, or saggital sections.

It should be understood that although the marker 100 is described above as being able to be left in place for any length of time or removed completely leaving no residual adhesive and without damage to the film or emulsion, the present invention is not limited to such. For example, in some embodiments, a marker may leave a small albeit insubstantial amount of residual adhesive and/or may result in a small albeit insubstantial degradation of the diagnostic image.

In addition, although the marker 100 includes a base (or substrate) 102 that comprises a clear, thin plastic sheet of an appropriate size and shape, the base is not limited to such. In addition, it should be understood that the base may comprise a single layer or a plurality of layers attached to one another.

In some embodiments, it may be desirable to provide the second portion of the base with color characteristics (e.g., blue, red, yellow) in order to further attract attention to the portion of the diagnostic image therebeneath.

It should also be understood that the marker of FIG. 1 includes many features, not all of which will be needed or employed in every embodiment of the present invention. Thus, some embodiments will comprise less than all of the features of the marker of FIG. 1. Moreover, although the marker of FIG. 1 provides various advantages, it should be understood that such advantages may not be needed and/or may not be provided in every embodiment.

In addition, as stated above, it should be understood that the marker features disclosed herein can be used in any combination.

Figure 3:
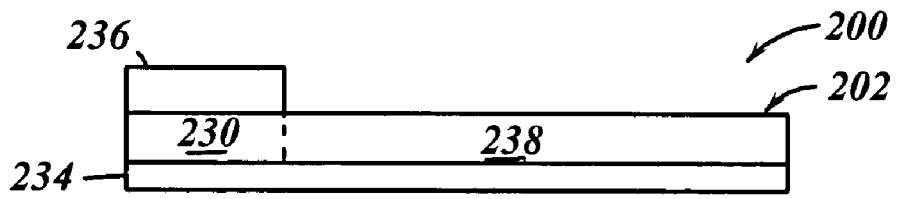
FIG. 3 shows a side elevational view of marker in accordance with a second embodiment.

FIG. 3 shows a side elevational view of a marker 200 according to a second embodiment. The marker 200 is similar to the marker 100 (except where otherwise noted, like reference numerals preceded by the numeral "2" instead of the numeral "1" are used to indicate like elements) except that the adhesive layer 234 of the marker 200 coats the underlying surfaces of both portions 230, 238 of the base 202. Thus, the adhesive layer 234 is preferably comprised of an adhesive that is substantially clear, and more preferably, transparent.

It should be understood that some other embodiments may employ adhesive on the underside of the second portion but not on the underside of the first portion.

Figure 4:
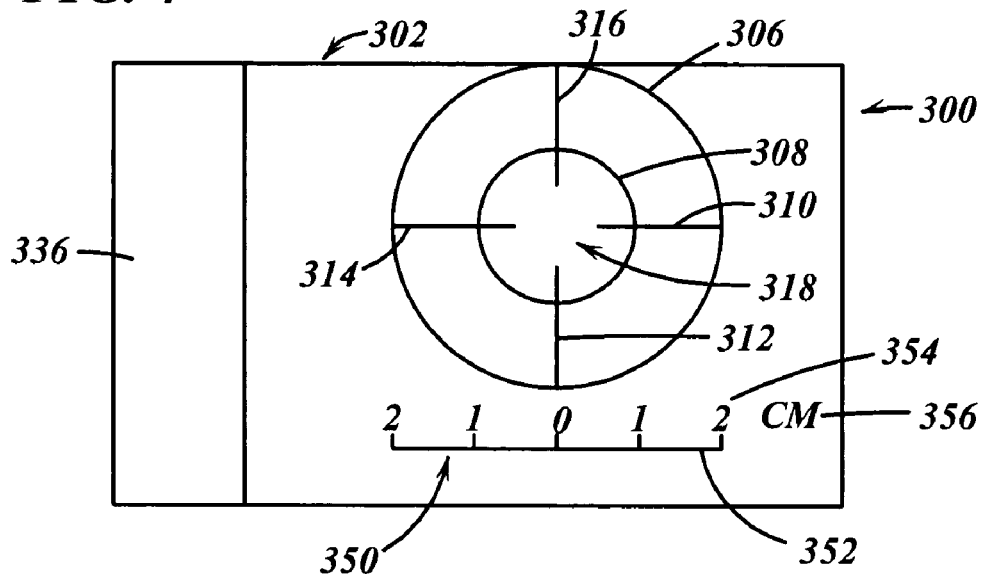
FIG. 4 shows an elevational view of a removable marker in accordance with a third embodiment.
Figure 5:
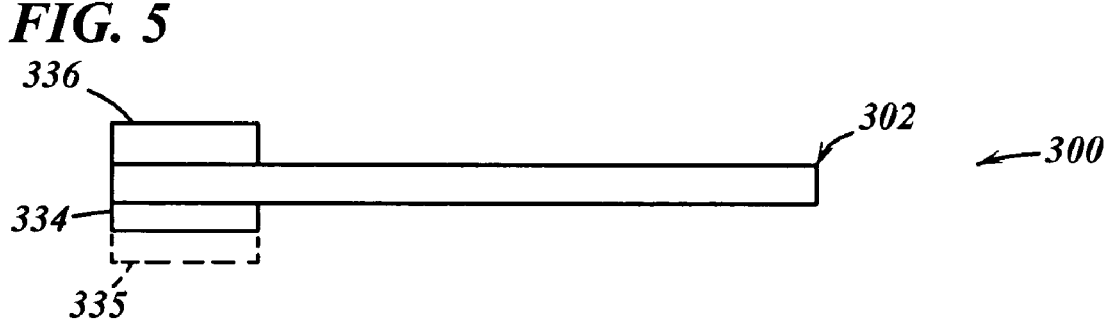
FIG. 5 shows a side elevational view of the marker of FIG. 4.

FIGS. 4–5 show views of a marker 300 according to a third embodiment. The marker 300 is similar to the marker 100 (except where otherwise noted, like reference numerals preceded by the numeral "3" instead of the numeral "1" are used to indicate like elements) except that (i) the base 302 and paper tab 336 of the marker 300 have square corners and are somewhat larger than the base 102 and paper tab 136, respectively, and (ii) the base 302 includes added indicia (compared to the base 102) in the form of a gauge portion 350. The larger base allows a border around the target sight, without the need to reduce the size of the target sight. The gauge portion 350 includes a graduated portion 352, numeric indicia 354 and dimensional indicia 356. This type of gauge portion may be used for example, to determine the size of features appearing in a diagnostic image (e.g., diagnostic image 120 (FIG. 2)). Gauge portions (or any portion thereof) may also be employed on the other markers disclosed herein.

The marker may be provided with a releasable backing 335 attached to the adhesive layer 334. Such a backing would need to be removed prior to releasably attaching the marker to an image.

Figure 6:
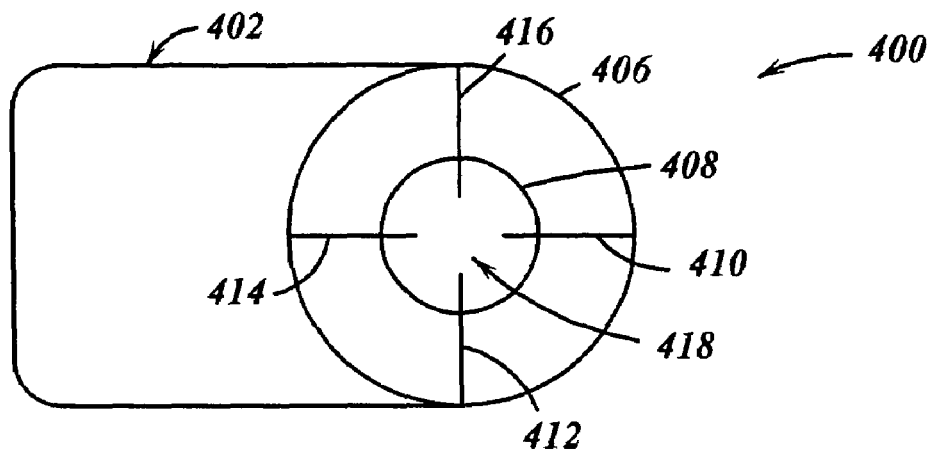
FIG. 6 shows an elevational view of a removable marker in accordance with another embodiment.
Figure 7:
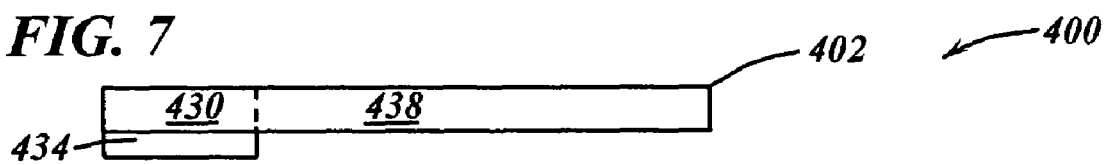
FIG. 7 shows a side elevational view of the marker of FIG. 6.

FIGS. 6–7 show views of a marker 400 according to a fourth embodiment. The marker 400 is similar to the marker 100 (except where otherwise noted, like reference numerals preceded by the numeral "4" instead of the numeral "1" are used to indicate like elements) except that the marker 400 does not include a plain paper tab for notes. The first base portion 430 is made translucent or opaque and adapted to receive written notes.

Figure 8:
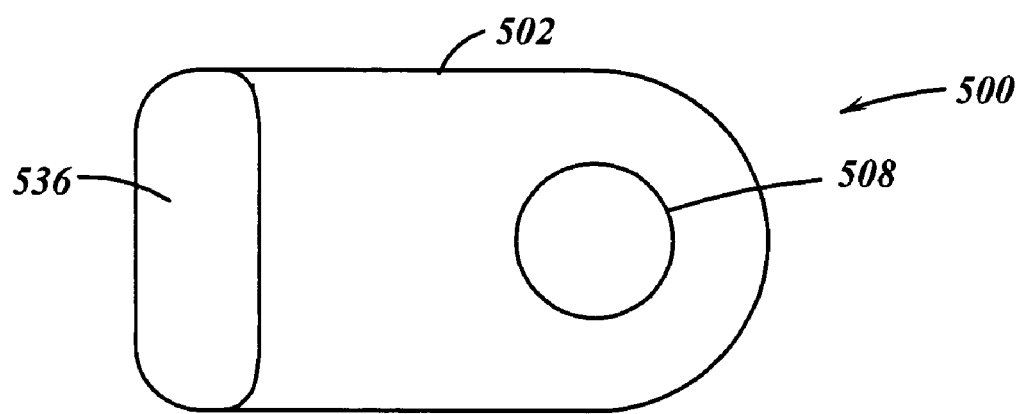
FIG. 8 shows an elevational view of a removable marker in accordance with another embodiment.
Figure 9:
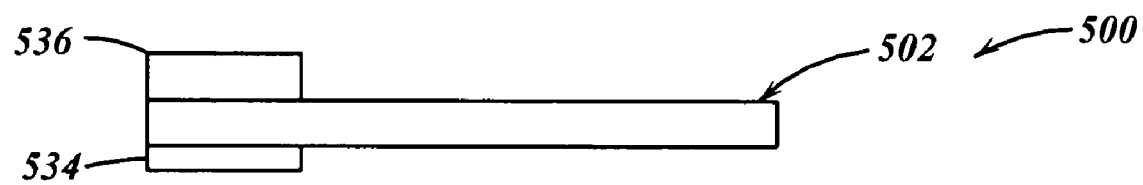
FIG. 9 shows a side elevational view of the marker of FIG. 8.

FIGS. 8–9 show views of a marker 500 according to a fifth embodiment. The marker 500 is similar to the marker 100 (except where otherwise noted, like reference numerals preceded by the numeral "5" instead of the numeral "1" are used to indicate like elements) except that the marker 500 has a target sight portion that includes one circle 508, rather than two, and does not include any cross hairs.

Figure 10:
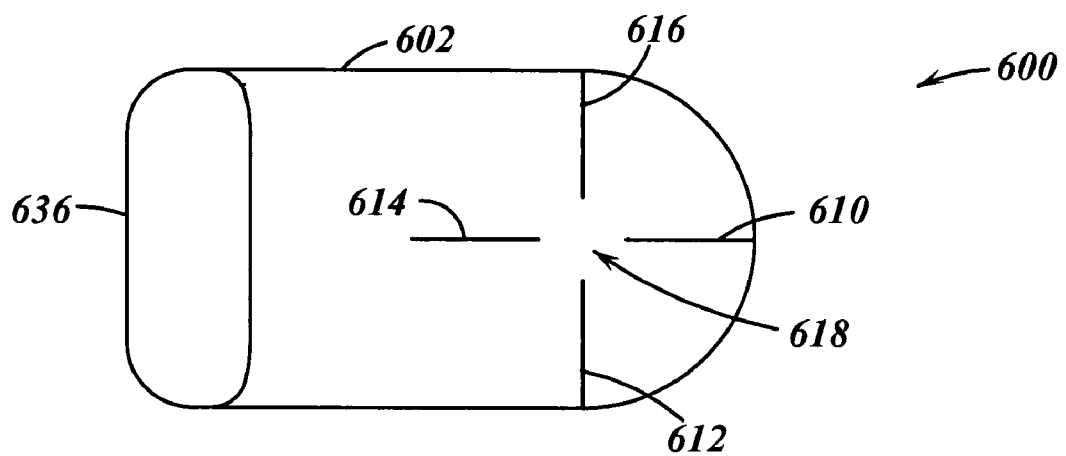
FIG. 10 shows an elevational view of a removable marker in accordance with another embodiment.
Figure 11:
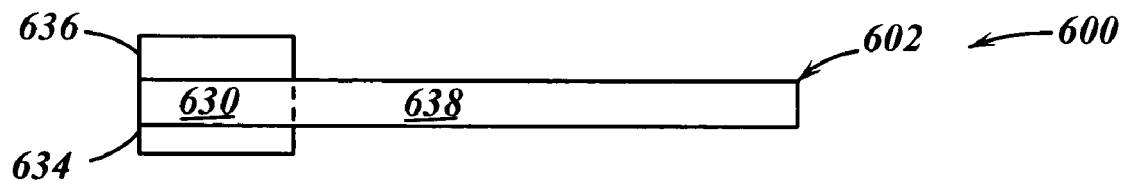
FIG. 11 shows a side elevational view of the marker of FIG. 10.

FIGS. 10–11 show views of a marker 600 according to a sixth embodiment. The marker 600 is similar to the marker 100 (except where otherwise noted, like reference numerals preceded by the numeral "6" instead of the numeral "1" are used to indicate like elements) except that the marker 600 has a target sight portion without concentric circles.

FIG. 12 shows a view of a marker 700 according to a seventh embodiment. The marker 700 is similar to the marker 100 (except where otherwise noted, like reference numerals preceded by the numeral "7" instead of the numeral "1" are used to indicate like elements) except that (i) the paper tab 736 of the marker 700 is somewhat larger than the paper tab 136 and (ii) the marker 700 includes indicia 760 to personalize the marker 700. In this embodiment, the personalized indicia indicates the name of a doctor and/or the name of a hospital, clinic, or school.

Figure 13:
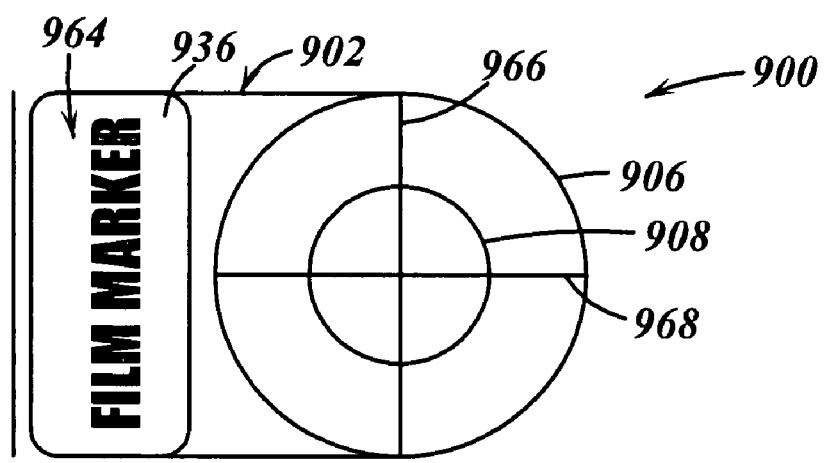

FIG. 13 shows a marker 900 according to another embodiment. The marker 900 is similar to the marker 100 (except where otherwise noted, like reference numerals preceded by the numeral "9" instead of the numeral "1" are used to indicate like elements) except that (i) the marker 900 has logo type indicia 964 and (ii) a target sight portion that includes crossing line segments 966, 968.

Figure 14:
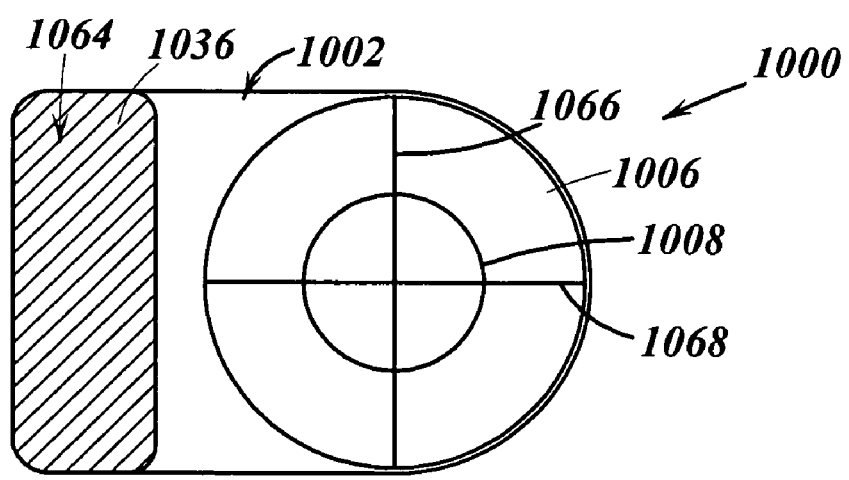

FIG. 14 shows a marker 1000 according to a another embodiment. The marker 1000 is similar to the marker 900 (except where otherwise noted, like reference numerals preceded by the numeral "10" instead of the numeral "9" are used to indicate like elements).

Figure 15:
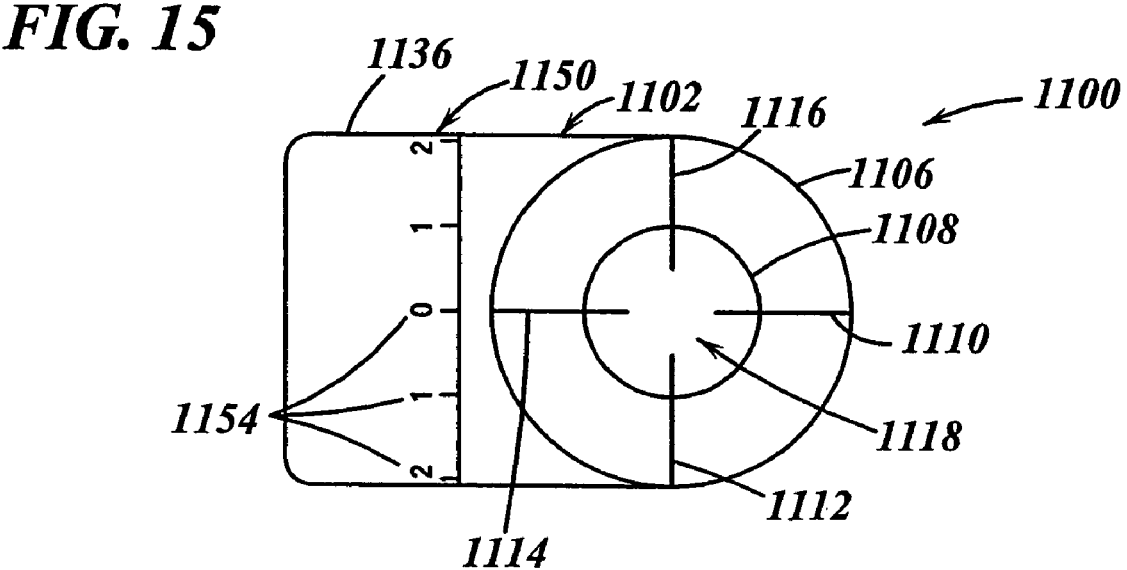

FIG. 15 shows a marker 1100 according to another embodiment. The marker 1100 is similar to the marker 100 (except where otherwise noted, like reference numerals preceded by the numeral "11" instead of the numeral "1" are used to indicate like elements) except that the marker 1100 includes indicia in the form of a gauge portion 1150. The gauge portion 1150 includes a graduated portion formed by numeric indicia 1154. This type of gauge portion may be used for example, to determine the size of features appearing in a diagnostic image (e.g., diagnostic image 120 (FIG. 2)). Similar or other type gauge portions (or any portion thereof) may also be employed on the other markers disclosed herein.

Figure 16:
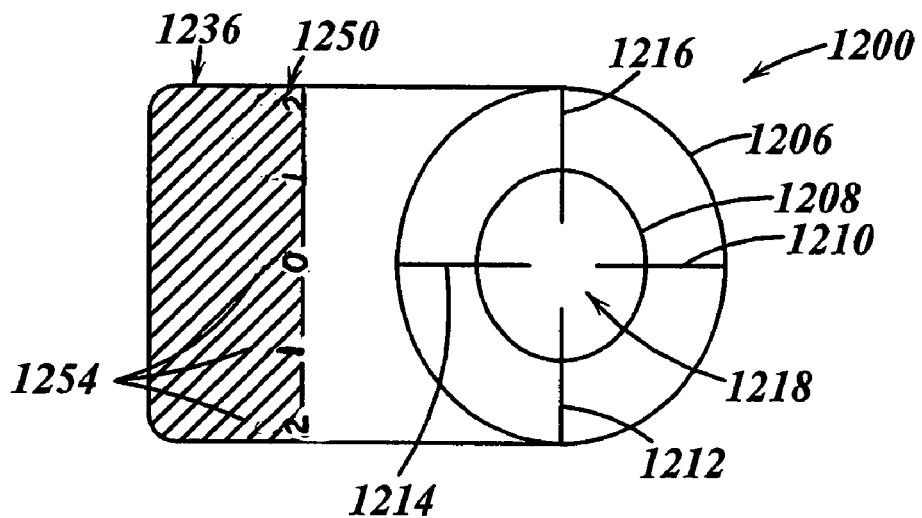

FIG. 16 shows a marker 1200 according to another embodiment. The marker 1200 is similar to the marker 1100 (except where otherwise noted, like reference numerals preceded by the numeral "12" instead of the numeral "11" are used to indicate like elements).

Figure 17:
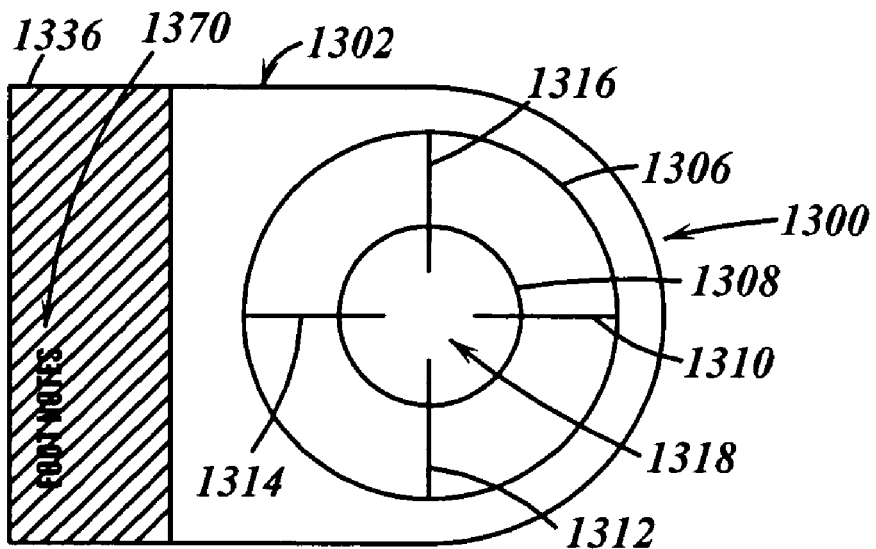

FIG. 17 shows a view of a marker 1300 according to another embodiment. The marker 1300 is similar to the marker 100 (except where otherwise noted, like reference numerals preceded by the numeral "13" instead of the numeral "1" are used to indicate like elements) except that (i) the base 1302 and the paper tab 1336 of the marker 1300 are somewhat larger than the base 102, and the paper tab 136, respectively, and (ii) the marker 1300 includes field of use indicia 1370 to indicate a field in which the marker 1300 may be used. Markers may of course be used in any field employing diagnostic images including but not limited to, for example, mammography, podiatry and dentistry. In this embodiment, the field of use indicia 1174 comprises the phrase "Foot Notes" which may for example be appropriate for use in association with podiatry.

Figure 18:
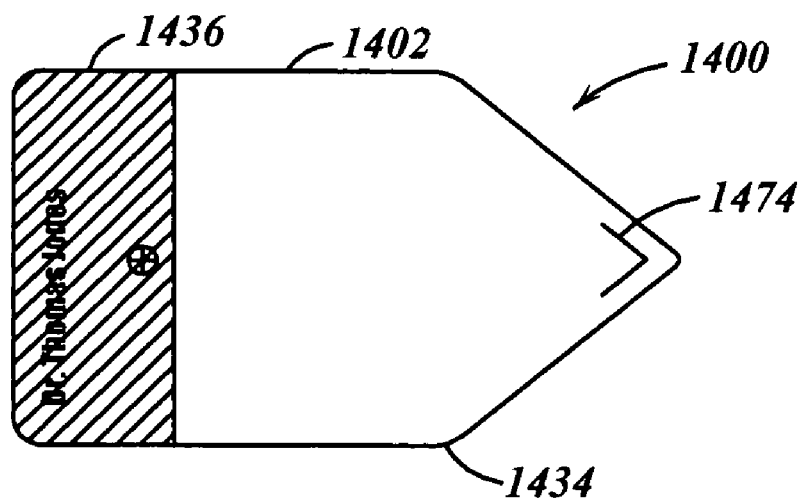

FIG. 18 shows a marker 1400 according to another embodiment. The marker 1400 is similar to the marker 700 (except where otherwise noted, like reference numerals preceded by the numeral "14" instead of the numeral "7" are used to indicate like elements) except that (i) the second base portion 1434 has an arrow-like shape, and (ii) the marker 1400 has a target sight portion that includes an arrow 1474 rather than concentric circles and cross hairs.

Figure 19:
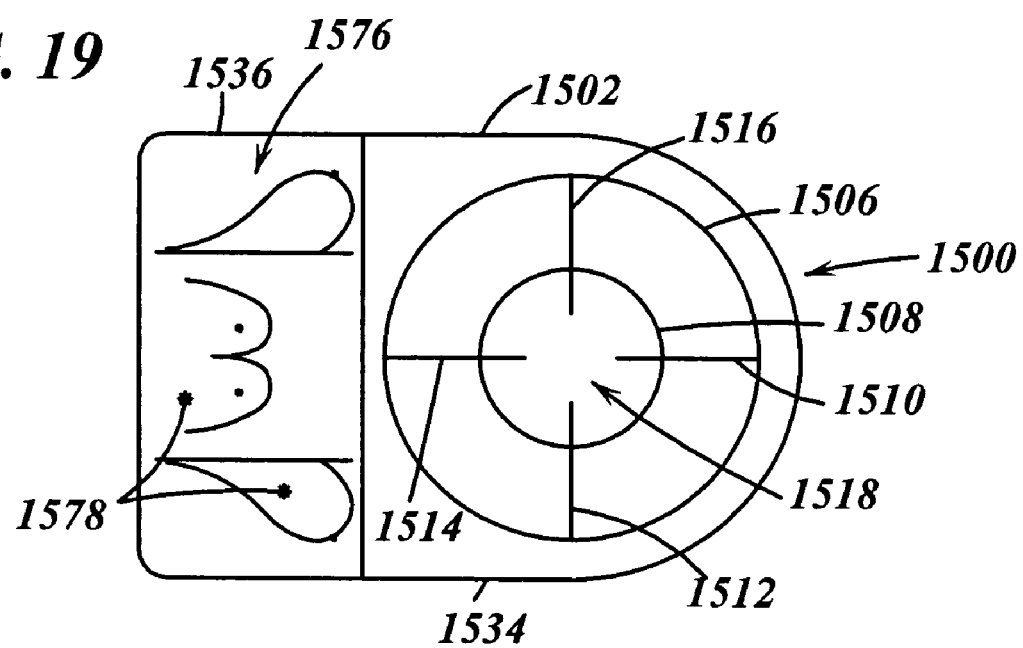

FIG. 19 shows a view of a marker 1500 according to another embodiment. The marker 1500 is similar to the marker 100 (except where otherwise noted, like reference numerals preceded by the numeral "8" instead of the numeral "1" are used to indicate like elements) except that (i) the base 1502 and the paper tab 1536 of the marker 1500 are somewhat larger than the base 102 and the paper tab 136, respectively, and (ii) the marker 1500 includes an anatomical indicia 1576, which in this embodiment includes a set of anatomical diagrams of two breasts. The diagrams can be marked 1578 to indicate the portion of the anatomical region that is depicted by the diagnostic image or within the target sight of the marker. This type of marker may be used in any diagnostic field, including but not limited to, for example, in association with diagnostic images that are generated using ultrasound technology.

Figure 20:
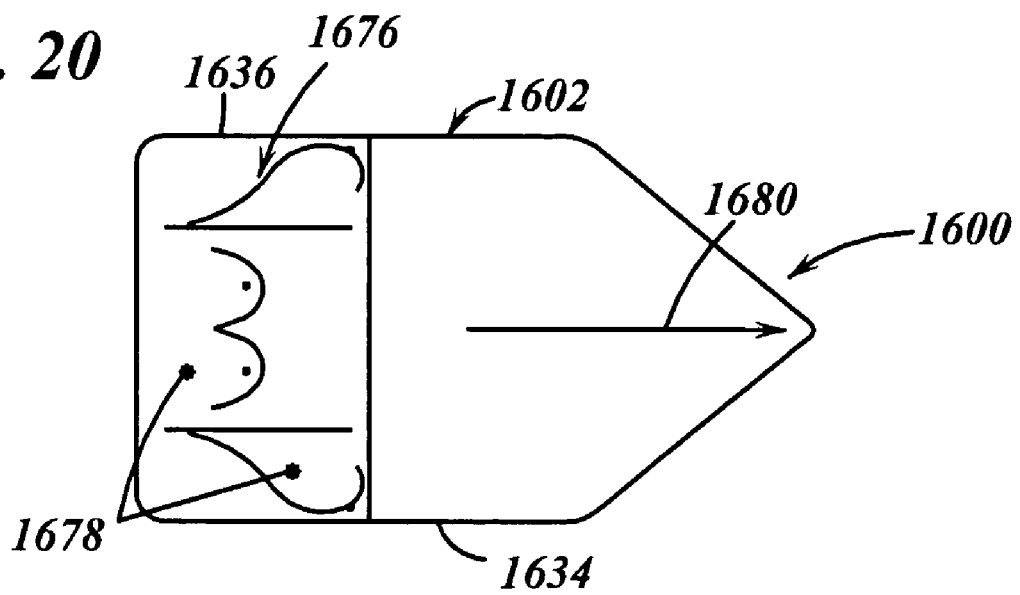

FIG. 20 shows a marker 1600 according to another embodiment. The marker 1600 is similar to the marker 1500 (except where otherwise noted, like reference numerals preceded by the numeral "16" instead of the numeral "15" are used to indicate like elements) except that (i) the second base portion 1634 has an arrow-like shape, and (ii) the marker 1600 has a target sight portion that includes an arrow 1680 rather than concentric circles and cross hairs.

Figure 21:
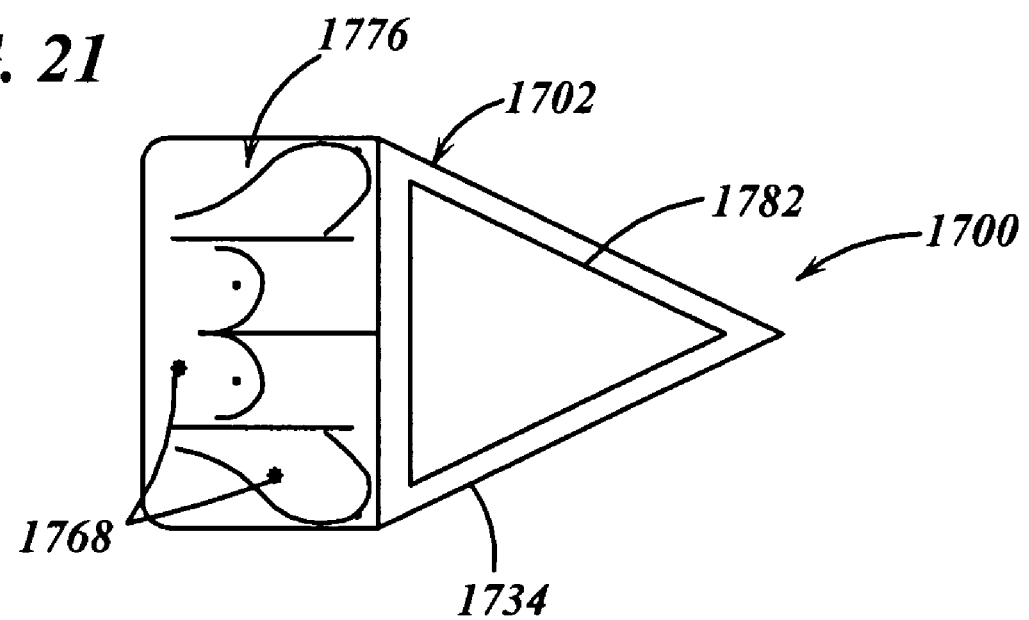

FIG. 21 shows a marker 1700 according to another embodiment. The marker 1700 is similar to some of the markers described above, however, the marker 1700 has a target sight portion that includes a triangle 1782.

Figure 22:
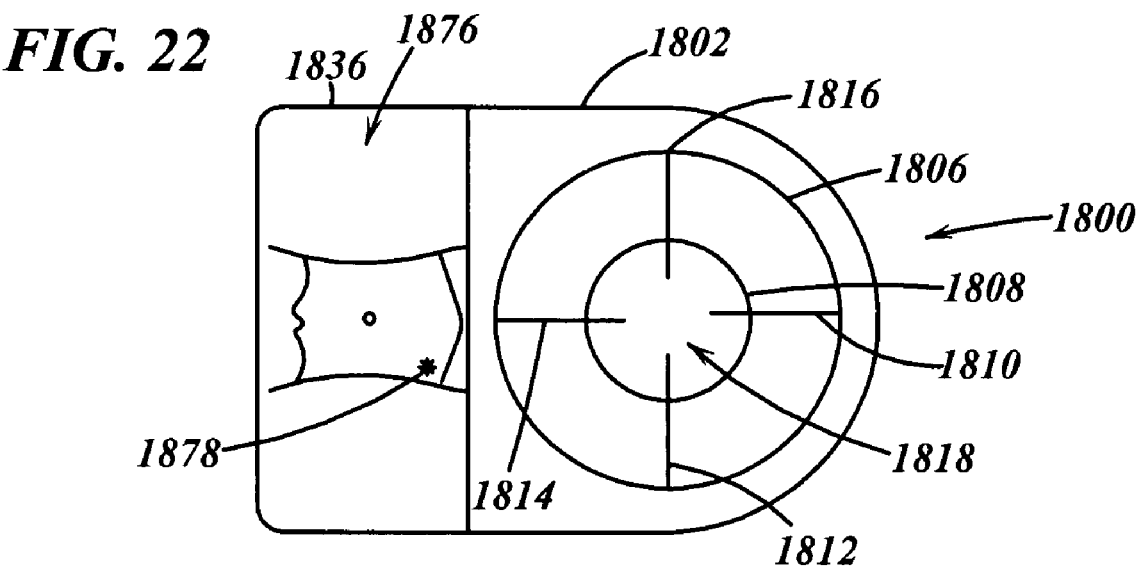

FIG. 22 shows a view of a marker 1800 according to another embodiment. The marker 1800 is similar to the marker 1500 (except where otherwise noted, like reference numerals preceded by the numerals "18" instead of the numerals "15" are used to indicate like elements) except that the marker 1800 includes anatomical indicia 1876, which in this embodiment includes an abdominal diagram. The diagram can be marked 1878 to indicate the portion of the abdominal region that is depicted by the diagnostic image or within the target sight of the marker. This type of marker may be used in any diagnostic field, including but not limited to, for example, in association with diagnostic images that are generated using ultrasound technology.

Figure 23:
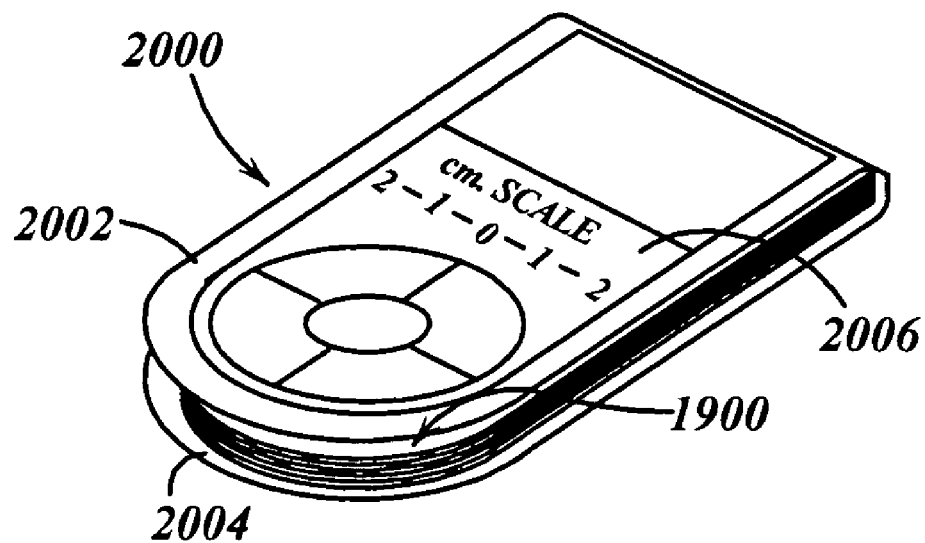
FIG. 23 shows a front perspective view of a holder in which removable markers may be mounted in accordance with one embodiment of another aspect of the present invention.

FIG. 23 shows a plurality of markers 1900 mounted within a holder 2000 having a form similar to that of a note pad. This holder 2000 comprises a strip formed of cardboard, plastic, or material(s) similar thereto. The strip is folded to define a front portion 2002, a back portion 2004, and a volume 2005 therebetween for mounting the markers 1900. The front and back portions 2002, 2004 may be similar in size and shape and may overlay one another as shown, although this is not required. The shape of the front and back portions may be similar to that of the markers 1900 mounted in the holder.

Figure 24:
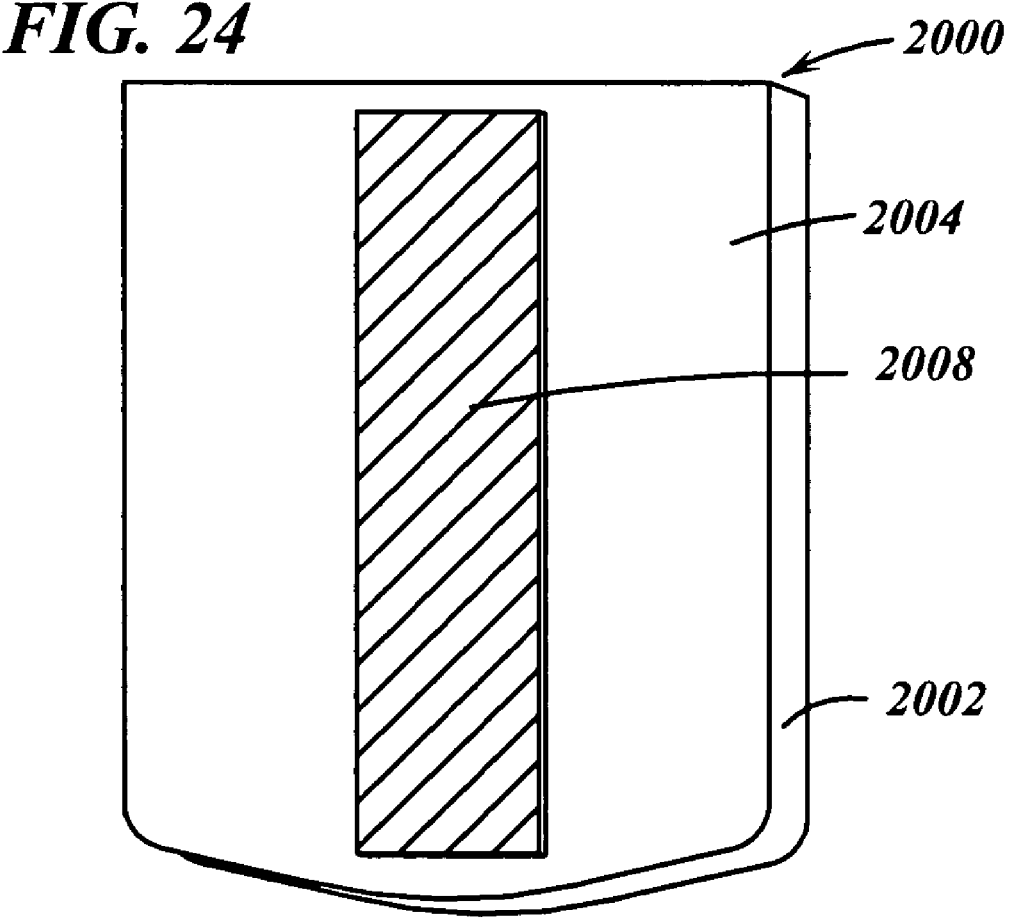
FIG. 24 shows a rear perspective view of the holder of FIG. 23.

The holder 2000 may further comprise a marker 2006 (or a simulated marker) and a double sided adhesive strip 2008 (FIG. 24). The marker 2006 (or simulated marker) may be affixed to the front portion 2002 of the holder 2000 and may have an appearance and orientation that is substantially identical to that of the plurality of markers 1900 mounted (or to be mounted) within the holder 2000. The double sided adhesive strip 2008 may be affixed to the rear portion 2004 of the holder to facilitate attachment of the holder 2000 to another structure.

This holder 2000 may for example hold approximately 20 to 50 removable markers. The markers 1900 are stacked one on top of the other, with the adhesive backing of each marker in the stack (except for the marker at the rear of the stack) attached to the front surface of an adjacent marker in the stack. The markers 1900 are each oriented with their adhesive backed portion adjacent to the folded portion of the holder 2000.

Some embodiments may replace the adhesive strip with another form of adhesive suitable to attach the holder to a desired structure. Some other embodiments may eliminate the adhesive on the rear portion 2004 altogether.

Figure 25A:
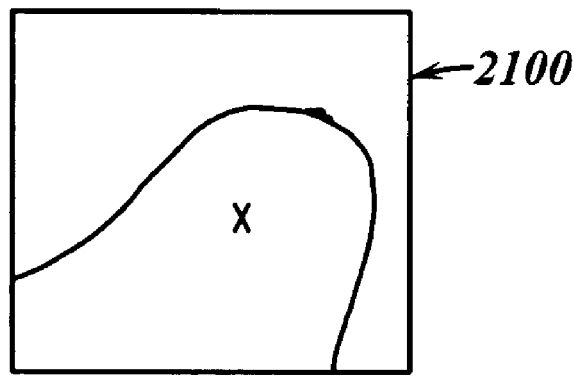
FIG. 25A shows a representation of a diagnostic image without a removable marker.
Figure 25B:
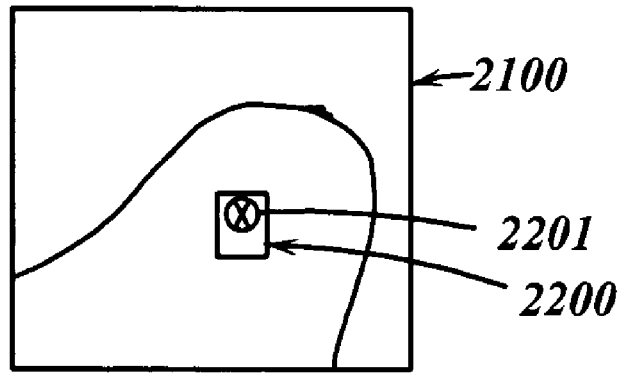
FIG. 25B shows a representation the diagnostic image of 25A with a removable marker attached thereto.
Figure 25C:
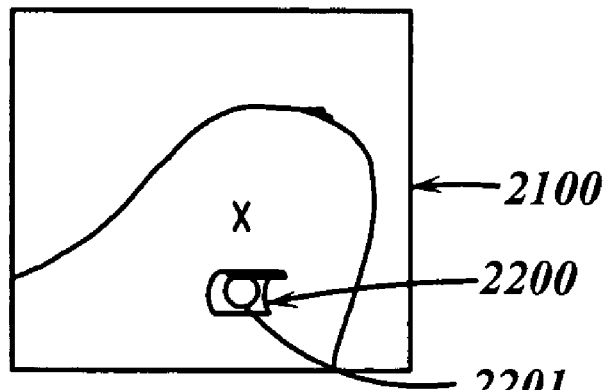
FIG. 25C shows a representation the diagnostic image of 25A with the removable marker of FIG. 25B attached thereto and one portion of the removable marker lifted to further reveal the area of concern beneath the target sight of the removable marker.

FIGS. 25A–25C show representations of a diagnostic image 2100 with and without a removable marker. More specifically, FIG. 25A shows a representation of a diagnostic image 2100 without a removable marker. The diagnostic image 2100 shows an image of a breast and has an area of concern designated by an "X". FIG. 25B shows a representation of a removable marker 2200 attached to the diagnostic image 2100. The removable marker 2200 has a target sight 2201 identifying the area of concern. FIG. 25C shows the removable marker 2200 attached to the diagnostic image 2100 but with one portion lifted to further reveal the area of concern beneath the target sight 2201 of the removable marker 2200.

In some embodiments, the marker has a target sight that includes some type of graduation system, such as for example, but not limited to, as shown in any one or more of FIGS. 1, 4, 6–8, 10, 12–17, 19, 22, 29–31, and 34–35. The marker may further include a text region that is to be displayed on the image and provides information regarding the marked region. In some embodiments, the system may actually require that the user supply information to be displayed in the text region and/or may cause the marker (or a portion thereof) to blink until such information is supplied.

Figure 26:
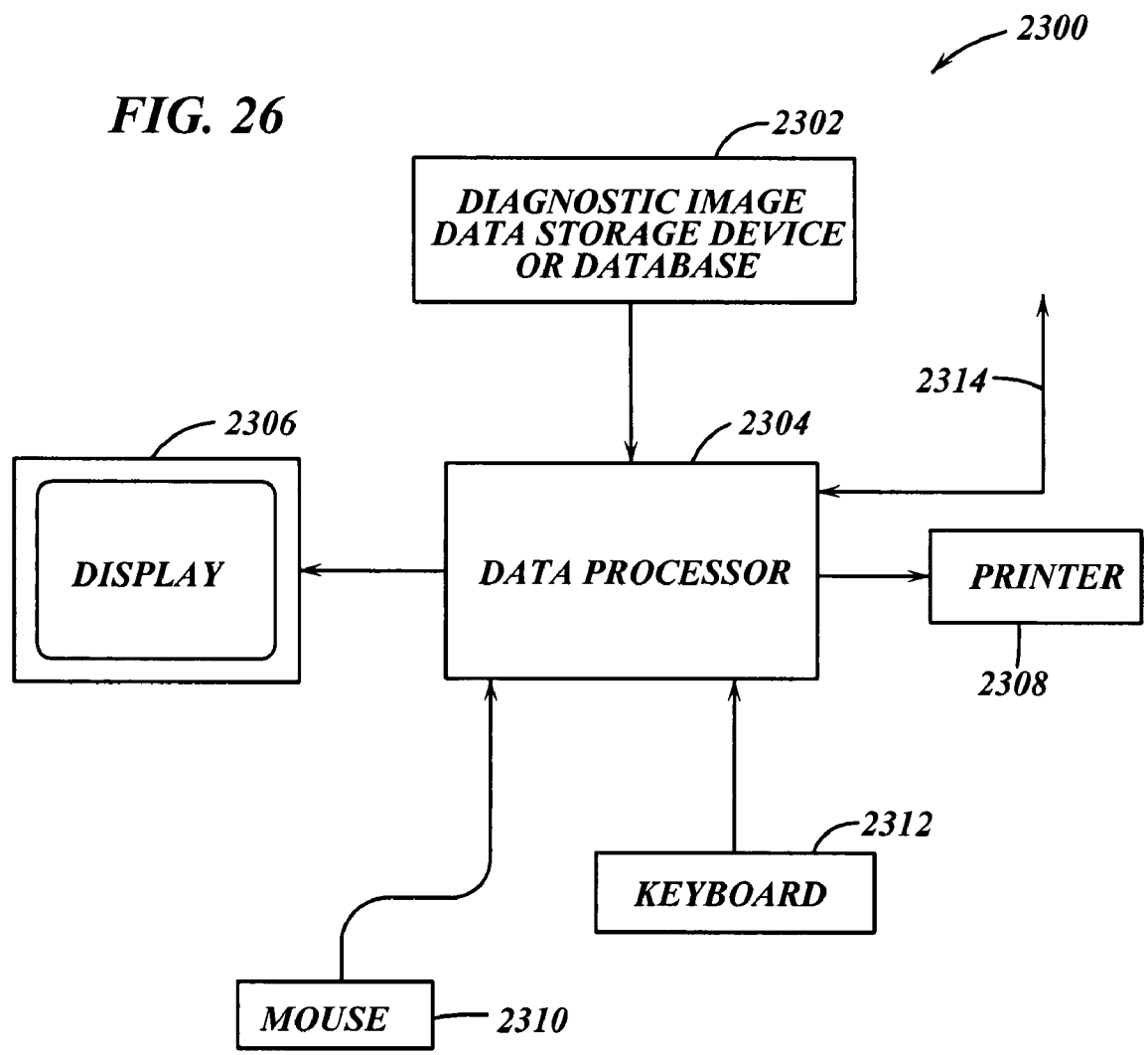
FIG. 26 shows a schematic block diagram of a system for adding and/or removing markers from digital diagnostic images in accordance with one embodiment of a third aspect of the present invention.

FIG. 26 shows schematic block diagram of a system 2300 for adding and/or deleting markers from digital diagnostic images in accordance with one embodiment of a third aspect of the present invention. This system is adapted to adding/removing marker(s) to/from a digital image that is recorded or displayed on a television screen, transmitted electronically, or portrayed on a computer monitor.

The system 2300 includes a diagnostic image storage device or database 2302, a data processor 2304, one or more output devices, e.g., a display 2306 and a printer 2308, one or more input devices, e.g., a mouse 2310 and a keyboard 2312, and a communication link 2314. The data processor 2304 may comprise for example, a digital computer having conventional elements including but not limited to a power supply, a central processor unit (CPU), volatile and nonvolatile storage elements, input/output subsystems, and operating system and application programs. The communication link 2314 may be any kind of communication link.

In operation, the storage device 2302 provides information indicative of a diagnostic image to the data processor 2304. The data processor 2304 in turn supplies an image to the display 2306 and/or printer 2308. The image supplied by the data processor may be, for example, the diagnostic image received from the storage device 2302 or the diagnostic image with one or more markers superimposed thereon. A user may employ one or more of the input devices, e.g., the mouse 2310 and/or the keyboard 2312, to provide information indicative of a location in the diagnostic image at which a marker is desired and/or information indicative of a marker to be removed from the image. The data processor 2304 responds to the information adding or removing a marker from the image that is supplied to the output device, e.g., the display 2306.

Figure 27A:
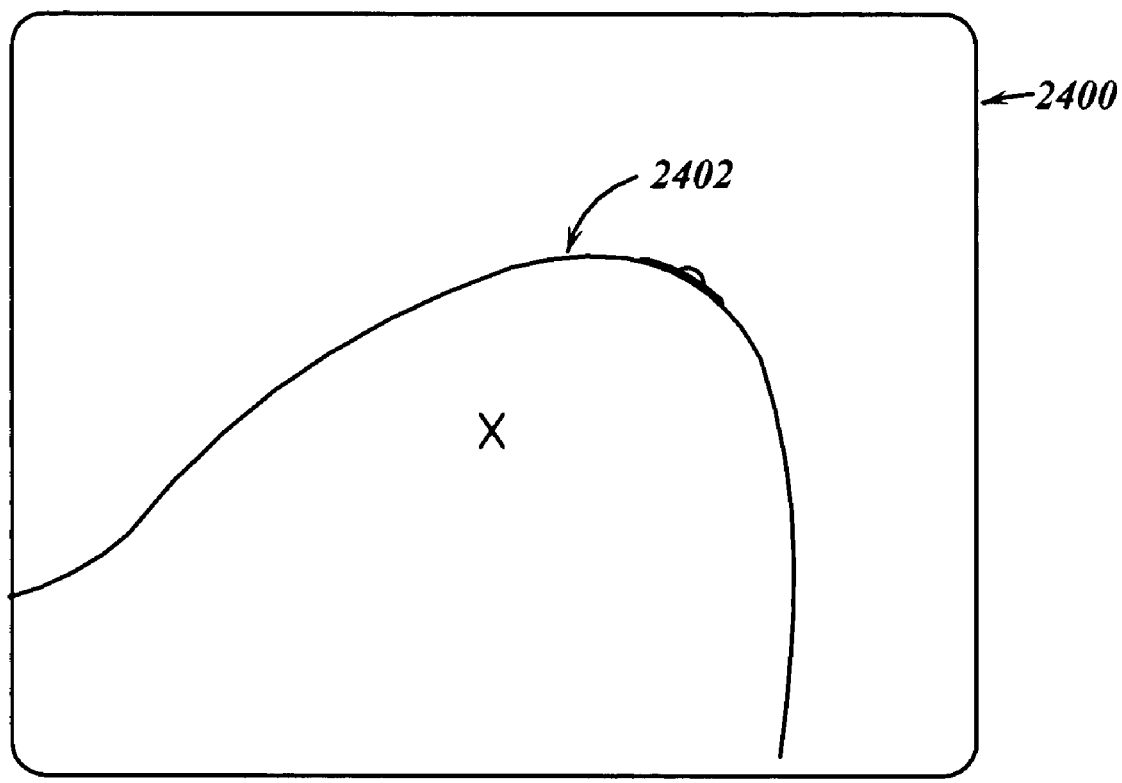
FIGS. 27A–27C show an example of the system of FIG. 26 adding a marker to a digital diagnostic image displayed on a display device.
Figure 27B:
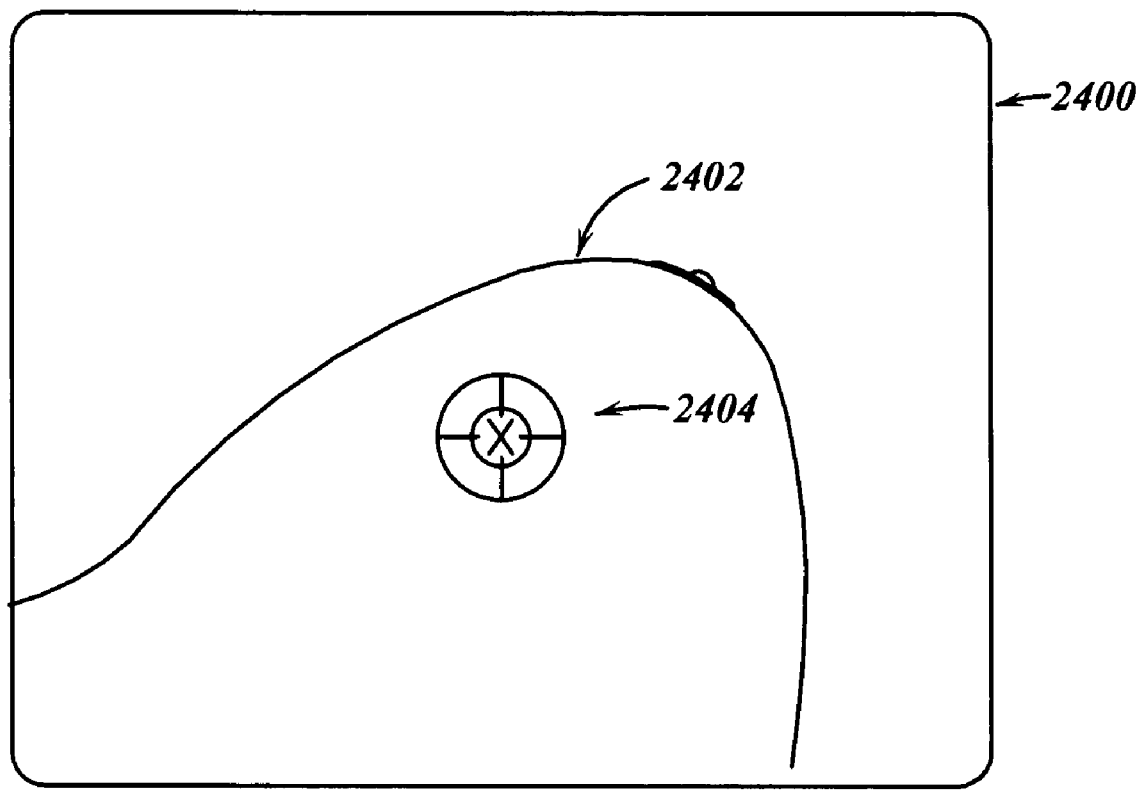
Figure 27C:
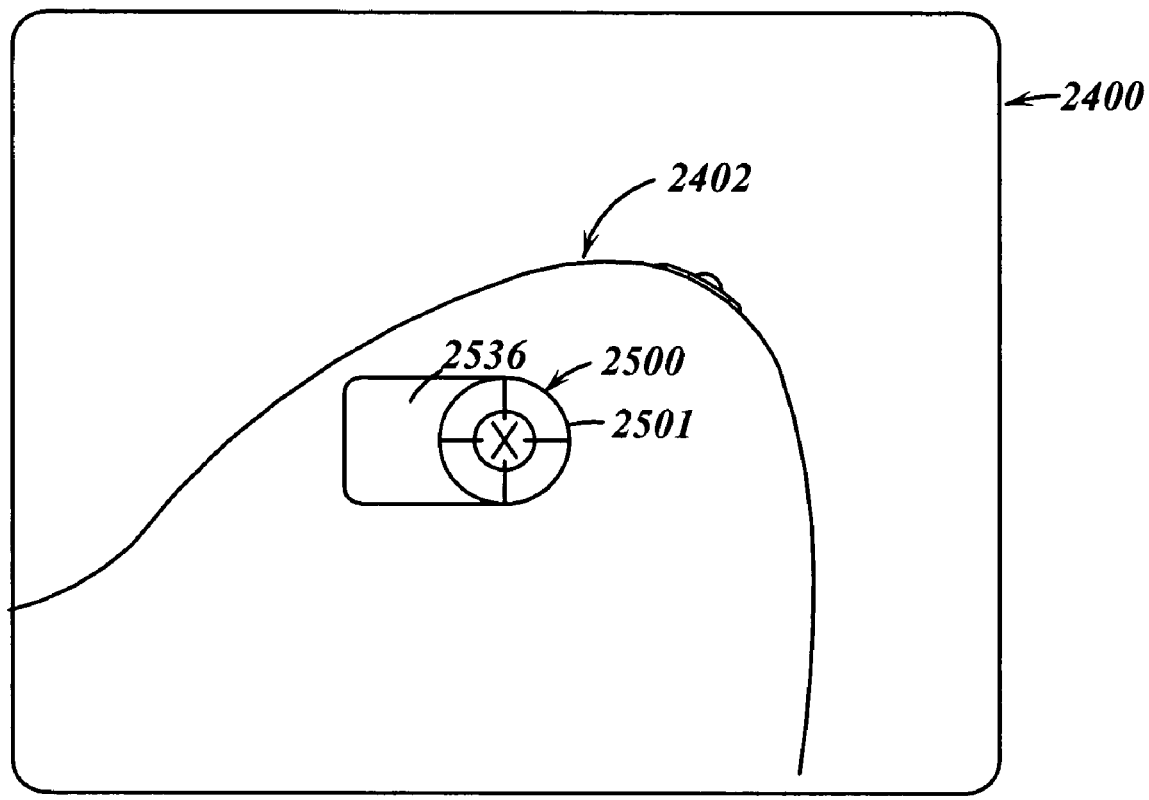

FIGS. 27A–27C show an example of adding a marker to a diagnostic image displayed on a display device, e.g., the display 2306. More specifically, FIG. 27A shows a representation of a diagnostic image 2400 without a marker. The diagnostic image 2400 includes an image of a breast 2402 and has an area of concern designated by an "X". FIG. 27B shows a representation of a target sight 2404 that is generated, for example, by the data processor 2304, and positioned so as to overlay the area of concern, for example, by the data processor 2304. In this embodiment, the positioning of the target sight 2404 within the image 2400 is carried out by the data processor 2304 in response to information (e.g., commands) from the user employing one or more of the input devices. FIG. 27C shows a representation of a marker 2500 that is generated, for example, by the data processor 2304, and positioned in accordance with the location of the target sight 2404 (FIG. 27B). The marker 2500 may for example, resemble one or more of the markers described hereinabove, although this is not required for the present invention. In this embodiment, the marker has a target sight 2501 that overlays the area of concern. The marker 2500 may further include a note portion 2536 for displaying other information (e.g., notes) although this is not required.

Figure 27D:
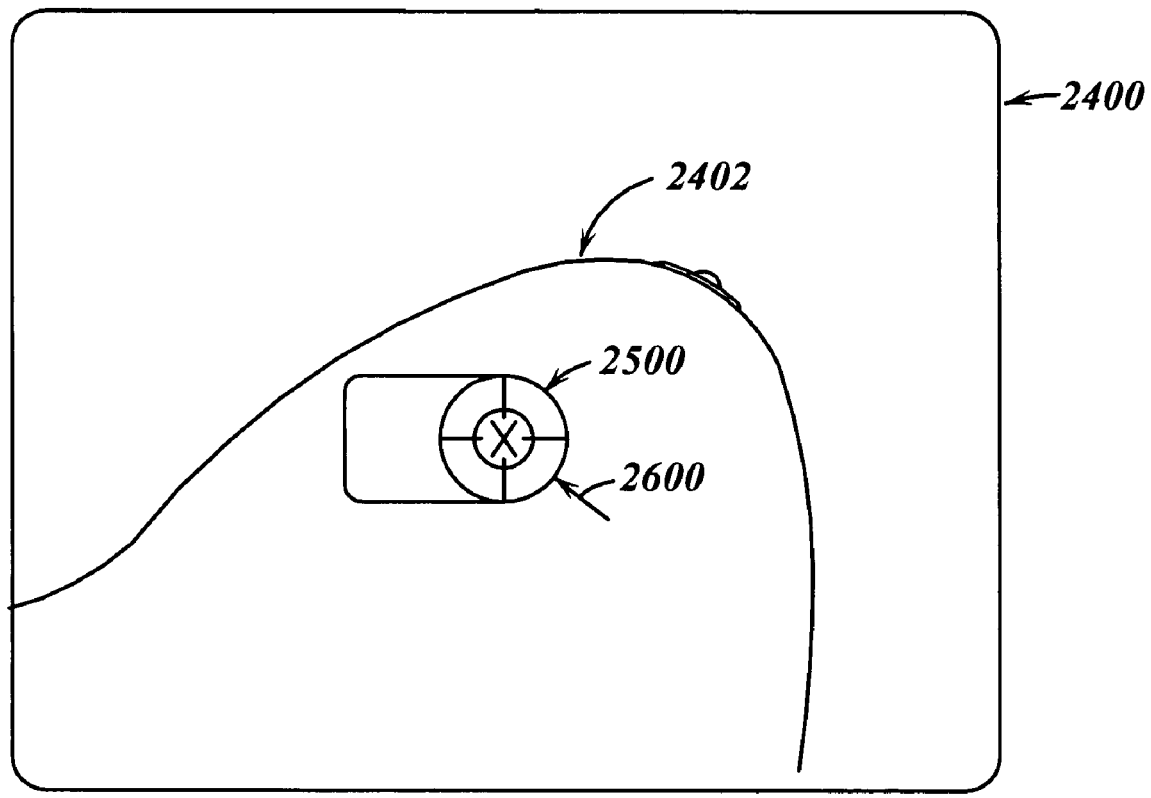
FIGS. 27D–27E show an example of the system of FIG. 26 removing a marker from a digital diagnostic image displayed on a display device.
Figure 27E:
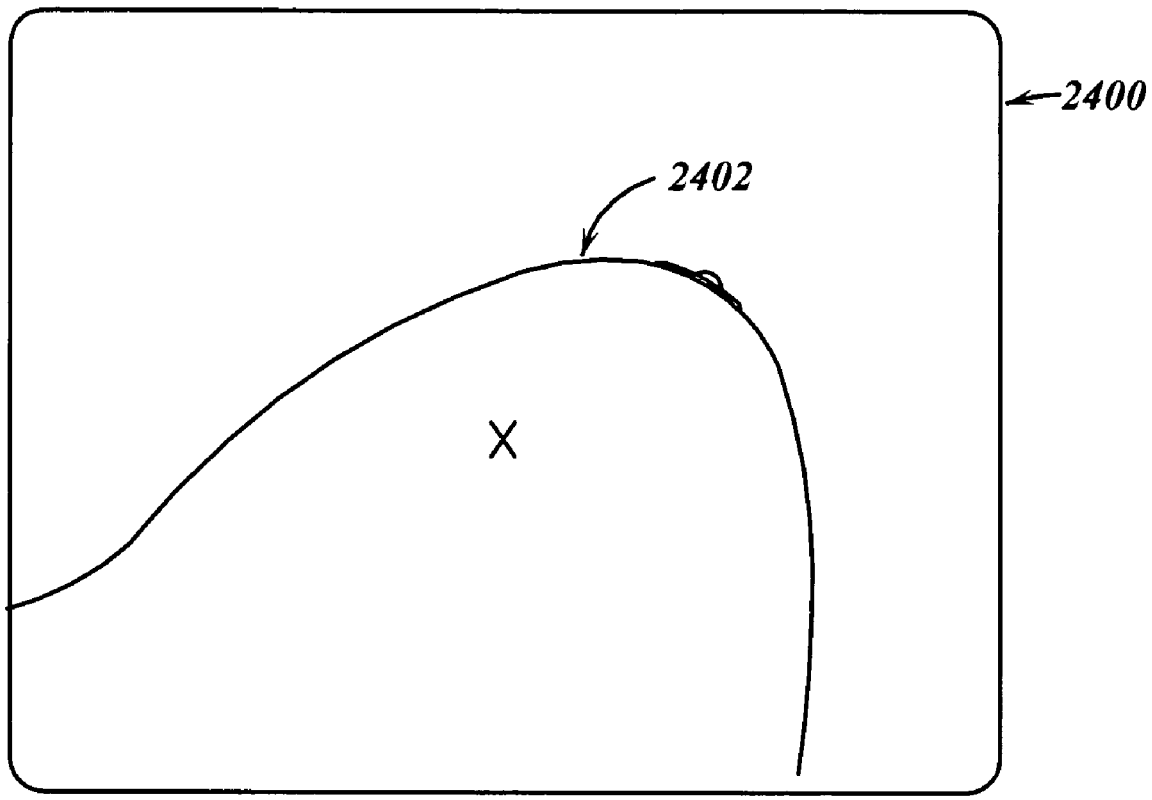

FIGS. 27D–27E show an example of removing the marker 2500 from the image. More particularly, FIG. 27D shows a pointer 2600 added to the image in response to information from the user. The pointer 2600 identifies the marker 2500 that is to be removed. In this embodiment, the positioning of the pointer 2600 within the image 2400 is carried out by the data processor 2304 (FIG. 26) in response to information from the user employing one or more of the input devices. It should be understood however that other methods may also be used for identifying a marker to be removed from the image 2400. FIG. 27E shows the image 2400 with the marker 2500 removed.

It should be understood that in some embodiments, the positioning of the marker may be carried out automatically in response to information from an image processor adapted to identify features of concern in the diagnostic image.

FIG. 28 is a flowchart 3000 showing steps carried out in one embodiment of the data processor, in association with adding and/or removing markers from a digital diagnostic image. At a step 3002, the data processor 2304 (FIG. 26) receives information representing a diagnostic image. At a step 3004, the data processor supplies an image to a display device, which displays the image. At a step 3006, the data processor receives information indicating the location of a marker to be added to the image and/or information indicating a marker to be removed from the image. At a step 3008, the data processor adds the marker at the indicated location, and/or removes the indicated marker from the image, as appropriate. At a step 3010, the data processor determines whether there are any more markers to be added or removed to/from the image. If there are no more markers to be added or removed, then execution proceeds to a step 3012, where the diagnostic image and marker information may be stored. Otherwise, execution reverts to the step 3006, to continue adding and/or removing markers to/from the image.

It should be understood that the data processor 2304 may be any kind of data processor. For example, the data processor may be programmable or non programmable, general purpose or special purpose, dedicated or non dedicated, distributed or non distributed, shared or not shared, and/or any combination thereof. A data processor may comprise hardware, software, firmware, hardwired circuits and/or any combination thereof. The data processor may or may not execute one or more computer programs that have one or more subroutines, or modules, each of which may include a plurality of instructions, and may or may not perform tasks in addition to those described herein. If the computer program includes more than one module, the modules may be parts of one computer program, or may be parts of separate computer programs. It should be recognized, that as used herein, the term module is not limited to a subroutine but rather may for example comprise hardware, software, firmware, hardwired circuits and/or any combination thereof.

In some embodiments, the data processor comprises at least one processing unit connected to a memory system via an interconnection mechanism (e.g., a data bus). A memory system may include a computer-readable and writeable recording medium. The medium may or may not be nonvolatile. Examples of non-volatile medium include a magnetic disk, flash memory, and magnetic tape. A disk may be removable, e.g., known as a floppy disk, or permanent, e.g., known as a hard drive. Examples of volatile memory include but is not limited to random access memory, e.g., dynamic random access memory (DRAM) or static random access memory (SRAM), which may or may not be of a type that uses one or more integrated circuits to store information. A variety of mechanisms are known for managing information movement between a disk and an integrated circuit memory element.

If the data processor executes one or more computer programs, the one or more computer programs may be implemented as a computer program product tangibly embodied in a machine-readable storage medium or device for execution by a computer. Further, if the data processor is a computer, such computer is not limited to a particular computer platform, particular processor, or programming language. Computer programming languages may include but are not limited to procedural programming languages, object oriented programming languages, and combinations thereof.

A general purpose computer system may or may not execute a program called an operating system, which may or may not control the execution of other computer programs and provides scheduling, debugging, input/output control, accounting, compilation, storage assignment, data management, communication control, and/or related services. A general purpose computer system may for example be programmable using a computer language such as C, C++, Java or other language, such as a scripting language or even assembly language. The computer system may also be specially programmed, special purpose hardware, or an application specific integrated circuit (ASIC).

As stated above, the communication link may be any kind of communication link including but not limited to, for example, wired (e.g., conductors, fiber optic cables) or wireless (e.g., microwave links, satellite links, infrared links), and combinations thereof, each of which may be public or private, dedicated and/or shared (e.g., a network). The communication link may employ for example circuit switching or packet switching or combinations thereof. Other examples of communication links include dedicated point-to-point systems, wired networks, and cellular telephone systems. The communication link may employ any protocol or combination of protocols including but not limited to the Internet Protocol.

Although mouse and keyboard input devices are shown, other types of input devices including but not limited to, tactile input devices such as a touch screens, may be employed.

Examples of output devices include, but are not limited to, cathode ray tube (CRT) devices, liquid crystal displays (LCD), plasma displays and other video output devices, printers, communication devices for example modems, storage devices such as a disk or tape and audio output, and devices that produce output on light transmitting films or similar substrates.

Although a display and printer output devices are shown, other types of output devices may be employed. Example input devices include but are not limited to keyboards, keypads, track ball, mouse, pen and tablet, light pen, touch screens, and data input devices such as audio and video capture devices.

It should thus be understood that the present invention is not limited to the input or output devices described herein.

FIG. 29 shows a marker 3100 according to another embodiment. The marker 3100 is similar to the marker 100 (except where otherwise noted, like reference numerals preceded by the numeral "31" instead of the numeral "1" are used to indicate like elements) except that the marker 3100 has a sticker 3190 with printed date indicia 3191. The date indicia 3191 indicates the date of the image and/or the date of the analysis of the image. Stickers such as the sticker 3190 are found in many clinics and laboratories. It should be understood however, that although the date indicia in this embodiment is provided in the form of a printed sticker, date indicia may added to a marker in any way.

FIG. 30 shows a marker 3200 according to another embodiment. The marker 3200 is similar to the marker 3100

(except where otherwise noted, like reference numerals preceded by the numeral "32" instead of the numeral "31" are used to indicate like elements) except that the marker 3200 has a base 3202 that is somewhat larger than the base 3102 to allow a border around the target sight 3201.

Figure 31:
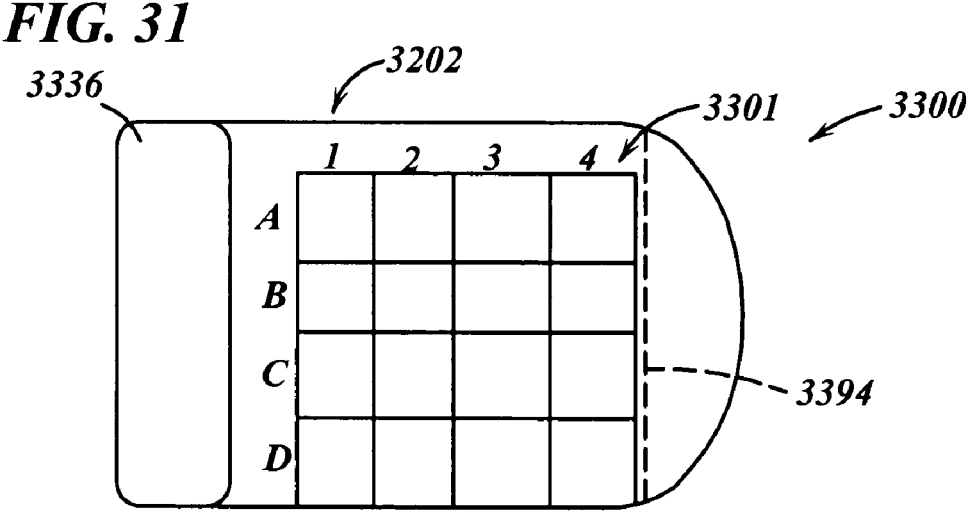

FIG. 31 shows a marker 3300 according to another embodiment. The marker 3300 is similar to the marker 100 (except where otherwise noted, like reference numerals preceded by the numeral "33" instead of the numeral "1" are used to indicate like elements) except that (i) the base 3302 is somewhat larger than the base 102 and (ii) the marker 3300 has a target sight that comprises a grid. The grid has a plurality of rows (e.g., labeled "A" through "D") and columns (e.g., labeled "1" through "4"). In some embodiments, the base may be squared off for example as indicated by dotted line 3394. Note that the target sight, as with many of the other target sights described herein can also serve as a gauge if dimensional indicia are provided or implied.

Figure 32:
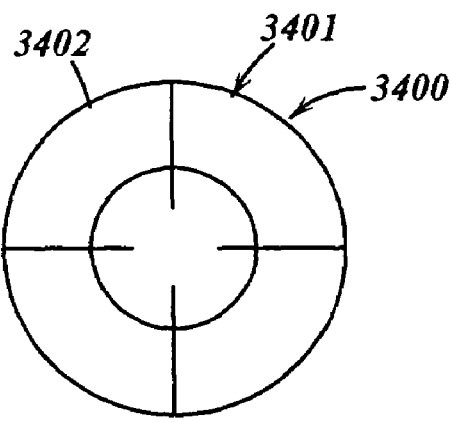

FIG. 32 shows a marker 3400 according to another embodiment. The marker 3400 is similar to the marker 100 (except where otherwise noted, like reference numerals preceded by the numeral "33" instead of the numeral "1" are used to indicate like elements) except that (i) there is no paper note portion and (ii) the base 3402 has substantially the same dimensions as the target sight.

Figure 33:
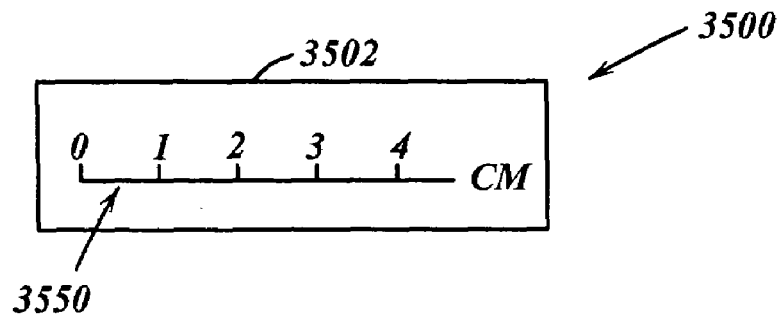

FIG. 33 shows a marker 3500 according to another embodiment. The marker 3500 is similar to the marker 300 (except where otherwise noted, like reference numerals preceded by the numeral "33" instead of the numeral "1" are used to indicate like elements) except that (i) there is no paper note portion and (ii) the gauge portion 350 also serves as the target sight for identifying a feature of interest.

FIGS. 34–55 show markers according to further embodiments. These markers are similar to the marker 3400 in that there is no paper note portion. In addition, it can be seen that the base of each marker is shaped to be slightly larger than the target sight of the marker, although even larger bases may be employed if desired.

Each of these markers has a base and a target sight. The base of each marker is transparent (or at least substantially transparent). Adhesive is disposed on the underlying surface of the base (at least a portion thereof). Thus, the adhesive layer 234 is preferably comprised of an adhesive that is substantially clear, and more preferably, transparent (or at least substantially transparent).

The markers of FIGS. 34–55 may be used, for example, to enhance images that are to be reproduced (e.g., copied) for publication and/or transmitted to another location. These markers may be particularly useful in the publication industry where it is desirable to have the ability to mark neatly mark an image. As can be seen, the markers can be any size and/or design.

FIGS. 34 and 35 show markers on which concentric circles are inscribed or printed on the substrate for use in marking an area of interest.

FIGS. 36–38 and 50–51 show a series of markers having a single circle inscribed or printed on the substrate. The circles on the markers may have varying sizes. For example, the markers shown in FIGS. 36–38 may have circles having diameters of 4 cm, 3 cm and 2 cm respectively while the markers in FIGS. 50–51 may be 1.0 cm and 0.5 cm respectively.

FIGS. 39–42 show markers having solid lined arrows inscribed or printed on the substrate. The arrows may have varying lengths, as shown in FIGS. 39–42, and may be, for example, 3 cm, 2 cm, 1 cm and 0.5 cm respectively.

FIG. 43 shows a marker with an image of a hand with a pointing finger inscribed or printed on the substrate.

FIGS. 44–46 show single lined arrowheads that may be inscribed or printed on the substrate. The arrowheads may have lengths of 1 cm to 3 cm or more. FIGS. 47–49 show arrowheads outlined with double lines inscribed or printed on the substrate. The arrowheads may have lengths of 1 cm to 3 cm or more.

FIGS. 52–54 show arrows outlined by dotted lines inscribed or printed on the substrate, while FIG. 55 shows an arrow outlined by a broken line inscribed or printed on the substrate. The arrows may have lengths of 1 cm to 3 cm or more.

Figure 56:
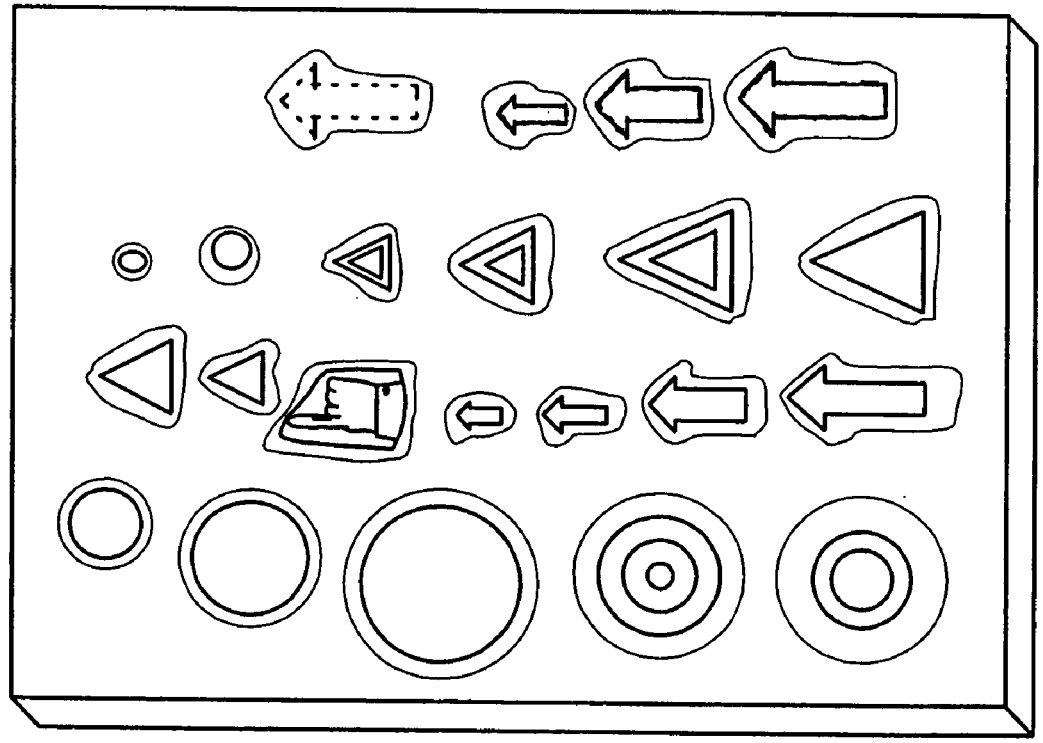
FIG. 56 shows a view of a plurality of removable markers fabricated on a sheet.

FIG. 56 shows one embodiment for fabricating removable markers on a sheet. The markers provided on the sheet would be removed (e.g., "peeled") off the sheet prior to use. The sheet has three layers: a marker base layer 4000, an adhesive layer 4002, and a backing. The marker is printed onto the base layer and the outline of the marker bases is punched into the marker base layer 4000 and the adhesive layer 4002 to enable the marker to be lifted or peeled off of the sheet. The backing comprises any suitable material that prevents the debris from sticking to the adhesive layer, yet allows the marker to be peeled off with the adhesive.

Figure 57:
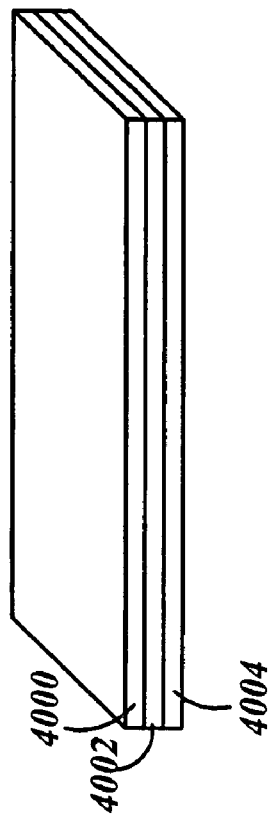
FIGS. 57–58 show side perspective and cross sectional views, respectively, of the removable markers fabricated on the sheet of FIG. 56.
Figure 58:
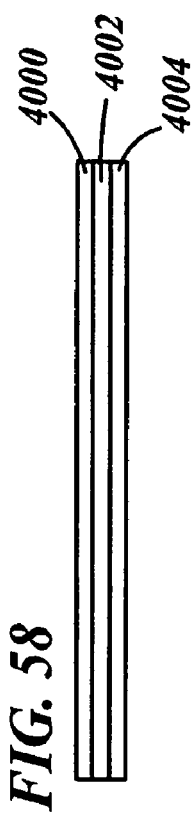

FIGS. 57, 58 shows side perspective and cross sectional views, respectively, of the removable markers mounted on the sheet of FIG. 56.

In view of the above, it should be understood that there is no requirement that the marker have a target sight. Nonetheless, it is desirable to have a target sight that focuses a readers attention on a region. Such target sights include but are not limited to, indicia that (i) substantially surround a region, (ii) extend in directions that converge at or toward a region, and/or (iii) point in directions that converge at or toward a region. As used herein, indicia that substantially surround a region include but are not limited to, indicia that are (i) on opposite sides of a region, (ii) extend in directions that converge at or toward a region, and/or (iii) point in directions that converge at or toward a region. As used herein, except where stated otherwise, the term substantially surrounds means at least substantially surrounds so as not to preclude actually surrounding a region.

As stated above, it should be understood that although many of the images described herein are diagnostic images, the various aspects of the present invention may be used in association with any type of image, unless explicitly stated otherwise. For example markers may be used in association with any type of image that conveys information and is to be analyzed, including but not limited to architectural or mechanical drawings, electrical schematics, photographs, and graphic art.

As to diagnostic images, it should be understood that although diagnostic images are widely employed within the medical fields, diagnostic images are also used is a wide variety of fields outside the medical field.

It should be understood that medical diagnostic images may be radiographic images and/or recorded anatomic images generated by other imaging modalities displayed on photographic film and/or other recording modalities. The markers described herein may be used with images generated by any diagnostic imaging modality.

It should be further understood that images may come in many forms and may for example be captured on a light transmitting substrate (e.g., x-ray film), plastic, paper or any other suitable medium. Unless explicitly stated otherwise, the various aspects of the present invention are not restricted to use in association with light transmitting substrates (e.g., x-ray films).

In addition, as stated above, it should be understood that the marker features disclosed herein can be used in any combination.

Note that, except where otherwise stated, terms such as, for example, "comprises", "has", "includes", and all forms thereof, are considered open-ended, so as not to preclude additional elements and/or features.

Also note that, except where otherwise stated, terms such as, for example, "in response to" and "based on" mean "in response at least to" and "based at least on", respectively, so as not to preclude being responsive to and/or based on, more than one thing.

While there have been shown and/or described various embodiments, it will be understood by those skilled in the art that the present invention is not limited to such embodiments, which have been presented by way of example only, and that various changes and modifications may be made without departing from the spirit and scope of the invention. Accordingly, the invention is limited only by the appended claims and equivalents thereto.

What is claimed is:

1. A marker for identifying or measuring details of an image provided on a light transmitting substrate, the marker comprising:
a substrate having at least one portion with an adhesive backing releasably engageable with the light transmitting substrate at an engaged position overlying at least a portion of the image, and further having at least one substantially transparent portion located laterally on the substrate with respect to the adhesive backing and overlying at least a portion of the image in the engaged position with at least a portion of the underlying image viewable therethrough, wherein the substantially transparent portion includes indicia thereon viewable with reference to at least a portion of the underlying image through the substantially transparent portion for identifying or measuring details of the underlying image.

2. The marker of claim 1 wherein the substrate comprises a first portion and a second portion, the first portion having a surface with an adhesive backing, the second portion being substantially transparent and having the indicia for identifying or measuring details of an image.

3. The marker of claim 2 wherein the indicia comprises a target sight.

4. The marker of claim 3 wherein the target sight focuses a readers attention on a region of the image.

5. The marker of claim 3 wherein the target sight substantially surrounds a region of the second portion.

6. The marker of claim 3 wherein the target sight comprises at least one circle.

7. The marker of claim 6 wherein the at least one circle comprises a circle having a diameter of about 1 cm.

8. The marker of claim 6 wherein the at least one circle comprises a circle having a diameter of about 2 cm.

9. The marker of claim 6 wherein the at least one circle comprises a circle having a diameter of about 4 cm.

10. The marker of claim 6 wherein the target sight further comprises at least two line segments that are disposed on one or more lines that substantially bisect the circle.

11. The marker of claim 10 wherein the note portion comprises a paper surface having a plurality of substantially parallel lines and being adapted to receive graphite, lead, or ink writing, and the indicia comprises an inscribed dimension and graduations disposed on the second portion.

12. The marker of claim 3 wherein the target sight comprises at least two orthogonal line segments.

13. The marker of claim 12 wherein the target sight comprises a square having side dimensions of about 1 cm.

14. The marker of claim 12 wherein the target sight comprises a grid having a plurality of squares having side dimensions of about 1 cm.

15. The marker of claim 2 wherein the target sight substantially defines a perimeter around a region of the second portion.

16. The marker of claim 2 wherein the second portion has a substantially adhesive free backing.

17. The marker of claim 2 wherein the marker comprises a note portion that is not transparent.

18. The marker of claim 17 wherein the note portion comprises a surface adapted to receive graphite, lead, or ink writing.

19. The marker of claim 17 wherein the note portion includes a plurality of substantially parallel lines.

20. The marker of claim 17 wherein the note portion overlays the first portion.

21. The marker of claim 17 wherein the note portion comprises a substantially opaque paper surface to receive writing.

22. The marker of claim 17 wherein the note portion comprises a paper surface having a plurality of substantially parallel lines and being adapted to receive graphite, lead, or ink writing.

23. The marker of claim 2 wherein the indicia comprises an inscribed dimension.

24. The marker of claim 23 wherein the inscribed dimension is disposed on the second portion.

25. The marker of claim 2 wherein the indicia comprises graduations.

26. The marker of claim 25 wherein the graduations are disposed on the second portion.

27. The marker of claim 2 wherein the indicia comprises an inscribed dimension and graduations disposed on the second portion.

28. The marker of claim 1 further comprising a releasable sheet disposed on the adhesive backing.

29. Apparatus comprising:
a holder; and
a plurality of markers as set forth in claim 1, releasably mounted in the holder.

30. A marker as defined in claim 1, wherein the indicia is substantially opaque.

31. Apparatus comprising:
a light transmitting substrate for providing an image;
a removable marker having a first portion with adhesive backing releasably attachable to the light transmitting substrate, and further having a second portion that is substantially transparent and without adhesive backing overlying at least a portion of the image of the substrate in an attached position with at least a portion of the image viewable therethrough, the second portion being manually engageable and movable relative to the substrate and first portion in the attached position for viewing the image other than through the substantially transparent portion and without lifting the adhesive backed portion from the substrate.

32. The apparatus of claim 31 wherein the image is a diagnostic image.

33. The apparatus of claim 31 wherein the light transmitting substrate is an x-ray film.

34. Apparatus fur use in diagnosis diagnostic imaging, the apparatus comprising:
   a light transmitting substrate for providing a diagnostic image; and
   a removable marker having a first portion with adhesive backing releasably attachable to the light transmitting substrate, and further having a second portion that is substantially transparent and overlies at least a portion of the image of the substrate in an attached position with at least a portion of the image viewable therethrough, the second portion having a target sight thereon viewable with reference to at least a portion of the underlying image through the second portion and enabling identification or measurement of at least a portion of the underlying image.

35. Apparatus comprising:
   a light transmitting substrate for providing an image; and
   a removable marker having a first portion with adhesive backing releasably attachable to the light transmitting substrate, and further having a second portion that is substantially transparent and overlies at least a portion of the image of the substrate in an attached position with at least a portion of the image viewable therethrough, wherein at least one of the first portion and the second portion includes a gauge portion viewable with reference to at least a portion of the underlying image through the second portion and enabling identification or measurement of at least a portion of the underlying image.

36. Apparatus comprising:
   a light transmitting substrate for providing an image; and
   a removable marker having a first portion including an adhesive backing releasably attachable to the light transmitting substrate and at least one substantially opaque, writable surface portion located on an opposite side of the marker relative to the adhesive backing and configured to receive writing thereon, and further having a second portion located laterally with respect to the first portion that is substantially transparent and overlies at least a portion of the image of the substrate in an attached position with at least a portion of the image viewable therethrough.

37. A method for marking an area of interest on a diagnostic image comprising the steps of:
   providing a light transmitting substrate having a diagnostic image;
   providing a marker comprising a substrate having a first portion and a second portion, wherein the first portion has a surface with an adhesive backing and the second portion is substantially transparent and has indicia thereon;
   releasably engaging the first position of the marker to the substrate and positioning the second portion of the marker over at least a portion of the image with at least a portion of the underlying image visible therethrough; and
   viewing at least a portion of the underlying image through the second portion, and at least one of identifying and measuring the underlying area of interest of the image with reference to the indicia.

38. A method as defined in claim 37, further comprising the steps of providing a marker further including a substantially opaque, writable surface; and manually writing on the writable surface diagnostic information pertaining to the area of interest of the underlying image.

39. A method as defined in claim 37, further comprising the steps of providing a marker further including indicia in the form at least one of a gauge and a target sight, viewing at least a portion of the underlying image through the second portion, and at least one of identifying and measuring the underlying area of interest of the image with reference to the indicia.

40. A marker for at least one of identification and measuring a diagnostic image provided on a light transmitting substrate, the marker comprising:
   a marker substrate having a first portion and a second portion located laterally on the marker with respect to the first portion, wherein the first portion has means for releasably adhering the marker substrate to the light transmitting substrate in an engaged position overlying at least a portion of the diagnostic image, and the second portion has means for at least one of identifying and measuring an area of interest on the underlying diagnostic image.

41. A marker as defined in claim 40, wherein the first portion further comprises means for manually writing thereon information concerning the area of interest on the underlying diagnostic image.

* * * * *